United States Patent
Kawano et al.

(10) Patent No.: US 10,429,287 B2
(45) Date of Patent: Oct. 1, 2019

(54) INTERFEROMETRIC METHOD FOR MEASURING A SIZE OF PARTICLE IN THE PRESENCE OF A GAP

(71) Applicant: OSAKA UNIVERSITY, Osaka (JP)

(72) Inventors: Makoto Kawano, Suita (JP); Hitoshi Watarai, Suita (JP); Nobutoshi Ota, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 165 days.

(21) Appl. No.: 15/114,667

(22) PCT Filed: Jan. 28, 2015

(86) PCT No.: PCT/JP2015/052334
§ 371 (c)(1),
(2) Date: Jul. 27, 2016

(87) PCT Pub. No.: WO2015/115471
PCT Pub. Date: Aug. 6, 2015

(65) Prior Publication Data
US 2016/0349165 A1 Dec. 1, 2016

(30) Foreign Application Priority Data

Jan. 28, 2014 (JP) ................ 2014-013161

(51) Int. Cl.
*G01N 15/02* (2006.01)
*G01J 9/02* (2006.01)
(Continued)

(52) U.S. Cl.
CPC .. *G01N 15/0205* (2013.01); *G01J 2009/0257* (2013.01); *G01N 2015/025* (2013.01); *G01N 2015/03* (2013.01); *G02F 2001/213* (2013.01)

(58) Field of Classification Search
CPC ......... G01N 15/0205; G01N 2015/025; G01N 2015/0233; G01N 2015/03; G01J 2009/0257; G01J 3/26; G02F 2001/213
See application file for complete search history.

(56) References Cited

U.S. PATENT DOCUMENTS 4,896,948 A * 1/1990 Dono ................. G02F 1/21
356/519
6,657,218 B2 12/2003 Noda
(Continued)

FOREIGN PATENT DOCUMENTS

JP 2002-206918 A 7/2002
JP 2003-332047 A 11/2003
(Continued)

OTHER PUBLICATIONS

International Search Report issued in PCT/JP2015/052334; dated Apr. 28, 2015.
(Continued)

*Primary Examiner* — Michael P LaPage
(74) *Attorney, Agent, or Firm* — Studebaker & Brackett PC

(57) ABSTRACT

An observation apparatus (100) includes an observing optical system (101) capable of obtaining an image of a measurement target present in a gap included in a device (1). One end of the gap included in the device (1) is wider than the other end thereof, and upon light beam irradiation to the device (1), an interference fringe appears in the gap. The observing optical system (101) irradiates the gap included in the device (1) with a plurality of light beams having different wavelengths to cause a plurality of interference fringes to appear in the gap. Then the observing optical system (101) obtains an image of the plurality of interference fringes.

20 Claims, 25 Drawing Sheets

(51) Int. Cl.
*G02F 1/21* (2006.01)
*G01N 15/00* (2006.01)

(56) References Cited

U.S. PATENT DOCUMENTS

| | | | |
|---|---|---|---|
| 6,995,893 B2 | 2/2006 | Kobayashi | |
| 2002/0045272 A1* | 4/2002 | McDevitt | B01L 3/0289 436/518 |
| 2002/0088928 A1 | 7/2002 | Noda | |
| 2002/0197622 A1* | 12/2002 | McDevitt | G01N 33/54366 435/6.12 |
| 2003/0236502 A1* | 12/2003 | De La Serna | A61M 5/28 604/196 |
| 2004/0109218 A1 | 6/2004 | Kobayashi | |
| 2006/0182659 A1* | 8/2006 | Unlu | G01N 21/0303 422/82.05 |
| 2008/0186504 A1* | 8/2008 | Kiesel | G01N 21/031 356/454 |
| 2008/0187011 A1* | 8/2008 | Kiesel | G01J 3/26 372/19 |
| 2009/0156917 A1* | 6/2009 | Martini | A61B 5/14532 600/341 |
| 2009/0243438 A1* | 10/2009 | Hamada | B41J 2/14233 310/358 |
| 2010/0225913 A1* | 9/2010 | Trainer | G01N 15/0205 356/338 |
| 2011/0222062 A1* | 9/2011 | Martini | G01N 21/05 356/417 |

FOREIGN PATENT DOCUMENTS

| | | |
|---|---|---|
| JP | 2007-110697 A | 4/2007 |
| JP | 4068581 B2 | 3/2008 |
| JP | 2012-020286 A | 2/2012 |
| JP | 2012-071464 A | 4/2012 |
| JP | 2013-190423 A | 9/2013 |
| JP | 2013-253875 A | 12/2013 |

OTHER PUBLICATIONS

International Preliminary Report on Patentability issued in PCT/JP2015/052334; dated Mar. 7, 2016.

Kawano et al.; Nano-Gap Magnetophoresis with Raman Spectroscopic Detection; Analytical Sciences; Dec. 2010; vol. 26; pp. 1211-1213.

Mogi et al; A microfluidic device for stepwise size-based capturing of suspended particles; Journal of Micromechanics and Microengineering; 2010; pp. 1-6.

An Office Action mailed by the Japanese Patent Office dated Apr. 23, 2019, which corresponds to Japanese Patent Application No. 2017-196720 and is related to U.S. Appl. No. 15/114,667 with English translation.

* cited by examiner

INTERFEROMETRIC METHOD FOR MEASURING A SIZE OF PARTICLE IN THE PRESENCE OF A GAP

TECHNICAL FIELD

The present invention relates to an observation apparatus, a device that is capable of being used in the observation apparatus, a method for producing the device, a method for measuring a particle size by using the device, a method for observing resistance of a particle by using the device, a method for causing chemical reaction of a particle by using the device, a method for preserving a particle by using the device, and an automatic observation apparatus for observing a particle by using the device.

BACKGROUND ART

A dynamic light scattering method and a microscopic observation method have been known as methods for measuring particle sizes of particulates. The dynamic light scattering method is used for measuring the particle sizes in nanoscales. The dynamic light scattering method measures the particle sizes through data analysis of intensity of scattered light obtained through laser light irradiation. The data analysis is performed based on the assumption that particles sizes are in normal distribution. However, it is unclear whether or not actual particle size distribution is in normal distribution. The microscopic observation method measures the particle sizes through image analysis performed on an individual particle basis. However, the microscopic observation method requires lots of efforts for the analysis.

To address a problem as described above, a particle size measurement method using a light interference phenomenon has been developed (see Non-Patent Literature 1). Non-Patent Literature 1 discloses a particle size measurement device used for particle size measurement of particulates. The particle size measurement device has two glass plates. The two glass plates are attached to each other at respective one ends thereof, thereby forming a wedge-shaped gap between the two glass plates. Distance between the two glass plates increases with an increase in distance from a position where the two glass plates are attached to each other at the respective one-ends thereof. Upon light beam irradiation to the particle size measurement device, an interference fringe repeatedly having a bright line and a dark line is caused to appear due to an interference phenomenon. Observation of the number of dark lines in the interference fringe provides the distance between the two glass plates. In particle size measurement, particulates targeted for the particle size measurement are delivered into the wedge-shaped gap. Each of the delivered particulates is trapped at a portion of the gap in accordance with a size of the particulate. A stop position of the particulate can be measured to obtain the particle size thereof.

CITATION LIST

Non-Patent Literature

[Non-patent Literature 1] Makoto Kawano, et al. "Nano-Gap Magnetophoresis with Raman Spectroscopic Detection", ANALYTICAL SCIENCES, November, 2010, Vol. No. 26, pp. 1211-1213.

SUMMARY OF INVENTION

Technical Problem

The inventors have developed a new technique of more accurate particle size measurement through earnest study on a particle size measurement method.

It is an object of the present invention to provide an observation apparatus capable of more accurately measuring a particle size and a device that is capable of being used in the observation apparatus. It is another object of the present invention to provide a particle size measurement method for measuring a particle size by using the device, a resistance observation method for observing resistance of a particle by using the device, a chemical reaction method for causing chemical reaction of a particle by using the device, a particle preservation method for preserving a particle by using the device, and an automatic observation apparatus for observing a particle by using the device.

Solution to Problem

An observation apparatus according to the present invention includes an observing optical system capable of obtaining an image of a measurement target present in a gap included in a device. The gap has one end and another end. The one end is wider than the other end. Upon light beam irradiation to the device, an interference fringe appears in the gap. The observing optical system has a function of irradiating the gap with a plurality of light beams having different wavelengths to cause a plurality of interference fringes to appear in the gap and obtaining an image of the plurality of interference fringes.

A device according to the present invention is used in the observation apparatus described above. The device includes: a first member, and a second member forming the gap together with the first member.

In an embodiment, the second member has a flow channel having an inclined surface. The gap including the flow channel is formed by superposing the second member on the first member in a manner such that the inclined surface faces the first member.

In an embodiment, the device further includes: a first height adjusting member that sets a height of the one end of the gap; and a second height adjusting member that sets a height of the other end of the gap to be lower than the height of the one end thereof.

In an embodiment, the gap has a height on the order of nanometers in the other end.

In an embodiment, at least part of surfaces forming the gap is subjected to surface modification.

In an embodiment, the device further includes a liquid absorbent substance provided outside of the other end of the gap.

A first method for producing the device according to the present invention includes the following: adjusting a height of one end of a to-be-processed member by a piezoelectric element to incline the to-be-processed member; and fabricating the second member by carrying out, at least once, cutting the to-be-processed member by moving a tool horizontally with respect to the inclined to-be-processed member to form the flow channel.

A second method for producing the device including the following: positioning a to-be-processed member in a liquid discharge region; and forming at least one of the first height adjusting member and the second height adjusting member by discharging a liquid to the to-be-processed member.

In an embodiment, the method for producing the device further includes cleaning at least portions of the first member and the second member forming the gap.

A particle size measurement method according to the present invention refers to a method for measuring a particle size of a particle by using the device described above, and includes the following: delivering the particle from the one end into the gap, moving the particle toward the other end, and trapping the particle in the gap; and measuring a particle size of the trapped particle based on the interference fringe caused to appear by the gap.

A resistance observation method according to the present invention refers to a method for observing resistance of a particle by using the device described above, and includes the following: delivering the particle from the one end into the gap and moving the particle toward the other end; and adding physical stress to the particle present in the gap or injecting a predetermined reactive fluid from the one end into the gap.

A chemical reaction method according to the present invention refers to a method for causing chemical reaction of a particle by using the device described above, and includes the following: delivering the particle from the one end into the gap and moving the particle toward the other end; and injecting a predetermined reactive fluid from the one end into the gap.

A particle preservation method according to the present invention refers to a method for preserving a particle by using the device described above, and includes the following: delivering the particle from the one end into the gap and moving the particle toward the other end; and covering the one end and the other end of the gap.

An automatic observation apparatus according to the present invention includes: an automatic injector, an observing optical system, and a conveyance mechanism. The automatic injector is arranged in correspondence with a predetermined solution injection position. The automatic injector injects a solution, including particles and a solvent, into the gap included in the device described above. The observing optical system is arranged in correspondence with a predetermined observation position. The conveyance mechanism conveys the device in a manner such that the gap stops at the solution injection position and then conveys the device in a manner such that the gap stops at the observation position.

Advantageous Effects of Invention

With an observation apparatus of the present invention, accuracy in particle size measurement improves. With a device of the present invention, a gap can be formed which can cause a plurality of interference fringes to appear. With a method for producing the device of the present invention, the device having the gap that can cause the plurality of interference fringes to appear can be produced. With a particle size measurement method of the present invention, particle size measurement of a particle can be realized. With a resistance observation method of the present invention, resistance of a particle against physical stress and resistance of a particle against a predetermined reactive fluid can be verified. With a chemical reaction method of the present invention, chemical reaction of a particle to a predetermined reactive fluid can be verified. With a particle preservation method of the present invention, a particle can be preserved in the device. With an automatic observation apparatus of the present invention, particle observation can be automated.

DESCRIPTION OF EMBODIMENTS

Figure 1:
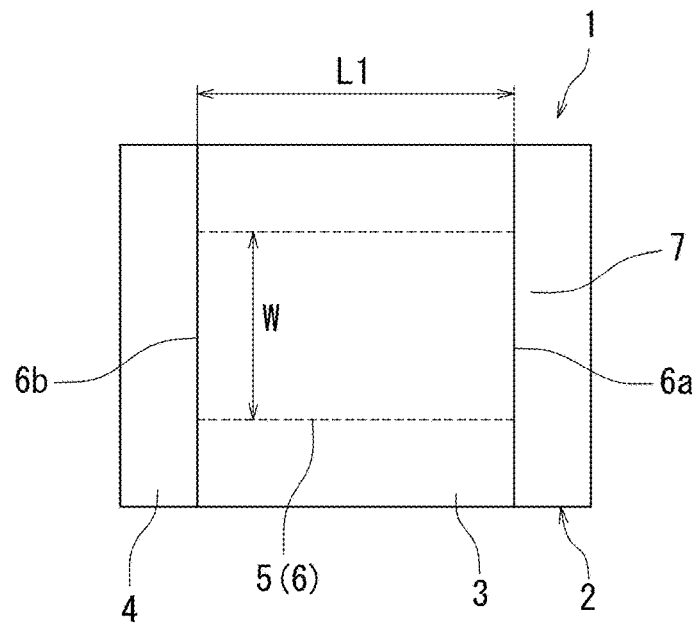
FIG. 1 is a top view schematically illustrating one example of a device according to a first embodiment of the present invention.

Hereinafter, the embodiments of the present invention will be described with reference to the drawings. Note that the present invention is not limited to the embodiments below. In the figures, the same or corresponding portions will be provided with the same reference numerals and description thereof will not be repeated. In addition, a material, a shape, dimension, etc. of each component shown in the embodiments below are each just one example and not at all limited, and various modifications may be made to the present invention within a range substantially not departing from the effects of the present invention.

(First Embodiment)

Figure 2:
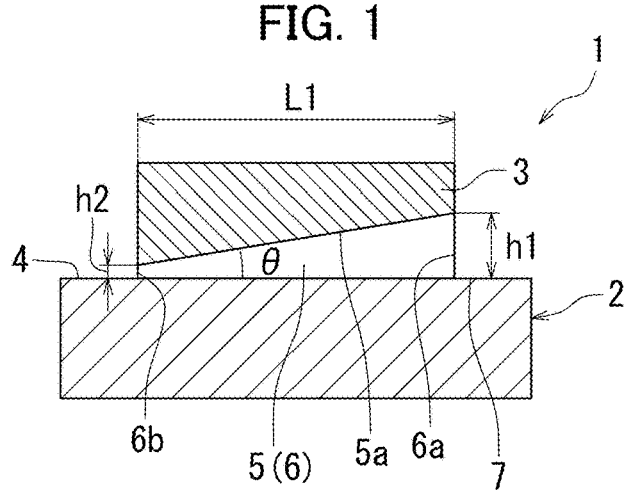
FIG. 2 is a cross-sectional view schematically illustrating one example of the device according to the first embodiment of the present invention.
Figure 3:
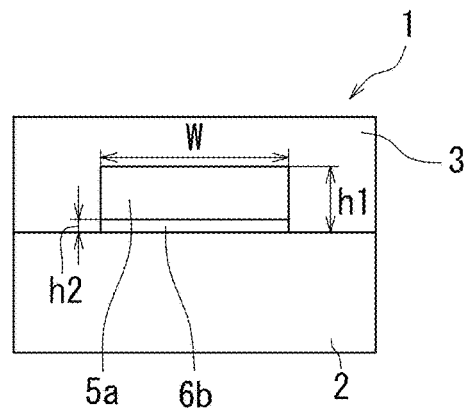
FIG. 3 is a front view schematically illustrating one example of the device according to the first embodiment of the present invention.

FIG. 1 is a top view schematically illustrating one example of a device 1 according to the first embodiment of the present invention, and FIG. 2 is a cross-sectional view schematically illustrating one example of the device 1 according to the first embodiment of the present invention. FIG. 3 is a front view schematically illustrating one example of the device 1 according to the first embodiment of the present invention. The device 1 will be described with reference to FIGS. 1 to 3. The device 1 includes a first plate-shaped member 2 as one example of a first member and a second plate-shaped member 3 as one example of a second member.

The first plate-shaped member 2 has a main surface 4 as a flat surface. The second plate-shaped member 3 has a groove 5 on a surface opposite to the main surface 4 of the first plate-shaped member 2. A bottom surface of the groove 5 is an inclined surface 5a. A portion of the surface of the second plate-shaped member 3 in contact with the main surface 4 of the first plate-shaped member 2 is a flat surface. The second plate-shaped member 3 is superposed and fixed on the first plate-shaped member 2 in a manner such that the inclined surface 5a faces the main surface 4 of the first plate-shaped member 2.

The device 1 has a gap 6 of a wedge shape between the inclined surface 5a and the first plate-shaped member 2. One end 6a and another end 6b of the gap 6 are open, and the gap 6 is so formed as to become continuously narrower from the one end 6a to the other end 6b. In the first embodiment, both ends of the groove 5 are open in a direction in which the inclined surface 5a is inclined, and openings of the one end 6a and the other end 6b of the gap 6 are formed of openings at the both ends of the groove 5.

Upon irradiation of a predetermined light beam to the device 1, an interference fringe is caused to appear by the gap 6. A material capable of causing such an interference fringe to appear is selected as a material of the first plate-shaped member 2 and the second plate-shaped member 3. For example, a glass plate or a plastic plate may be used as the material of the first plate-shaped member 2 and the second plate-shaped member 3. For example, an acrylic resin may be used as a material of the plastic plate. The same material may not be used for the first plate-shaped member 2 and the second plate-shaped member 3. Since it is only required to cause an interference fringe to appear by the gap 6, a material capable of causing an interference fringe only in a region corresponding to the gap 6 may be used. In addition, a material may be used which is capable of causing an interference fringe to appear upon irradiation of a predetermined light beam from the outside of one of the first plate-shaped member 2 and the second plate-shaped member 3. In the first embodiment, it is only required to cause an interference fringe to appear upon irradiation of a predetermined light beam from the outside of the second plate-shaped member 3.

The gap 6 of the device 1 can be used as a flow channel of fluids such as liquids or gas. In the first embodiment, the first plate-shaped member 2 has a longer length than the second plate-shaped member 3 in the direction in which the inclined surface 5a is inclined, and of the main surface 4 of the first plate-shaped member 2, an outer portion of the one end 6a of the gap 6 is used as a solution introduction part 7. Upon dripping of a solution including particulates and a solvent to the solution introduction part 7, the solvent is sucked into the gap 6 through a capillary action. The device 1 moves the particulates toward a narrow side (the other end 6b) of the gap 6 by using, as a driving force, a force for sucking the solvent into the gap 6 through the capillary action. As a result of injection of the solution, including the particulates and the solvent, from the opening in the one end 6a of the gap 6 into the gap 6, the particulates are trapped at portions of the gap 6 in accordance with sizes of the respective particulates.

No limitation is placed on a length L1 and a width W (see FIG. 1) of the gap 6 in a plan view of the device 1, but are preferably set at such dimensions that permit observation of the entire gap 6 on a microscope at a time. Setting the length L1 and the width W of the gap 6 at such dimensions makes it possible to observe all the particulates in the gap 6 at a time. For example, in a case where a microscope fitted with a 20-fold objective lens is used to photograph the gap 6, setting both the length L1 and the width W of the gap 6 within 1 mm makes it possible to capture the entire gap 6 on one screen without horizontally moving the screen.

A height h1 of the opening in the one end 6a of the gap 6 (an inlet of the flow channel) and a height h2 of the opening in the other end 6b of the gap 6 (an outlet of the flow channel) are in accordance with a size of a target particulate to be trapped in the gap 6 (see FIGS. 2 and 3). For example, the height h1 of the opening in the one end 6a of the gap 6 is 50 nm, and the height h2 of the opening in the other end 6b of the gap 6 is 10 nm.

Figure 4A:
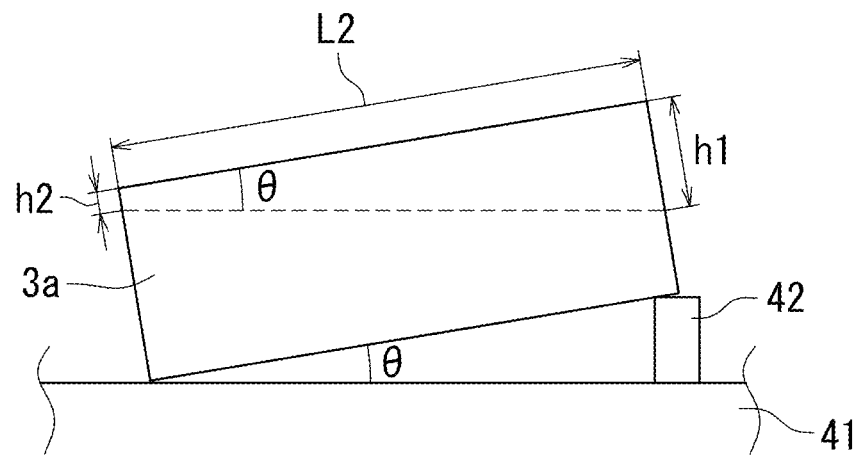
FIG. 4A is a schematic view illustrating a process of adjusting inclination of a plate-shaped member according to the first embodiment of the present invention.
Figure 4B:
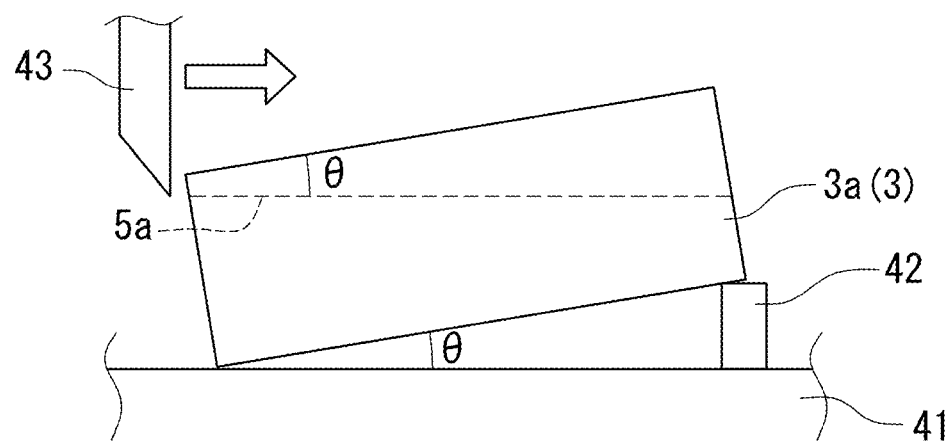
FIG. 4B is a schematic view illustrating a process of cutting the plate-shaped member according to the first embodiment of the present invention.

Next, one example of a method for producing the device 1 will be described with reference to FIGS. 4A and 4B. More specifically, one example of a method for fabricating the second plate-shaped member 3 according to the first embodiment of the present invention will be described. FIG. 4A illustrates a process of adjusting inclination of a plate-shaped member (one example of a to-be-processed member) 3a, and FIG. 4B illustrates a process of cutting the plate-shaped member 3a.

Upon the fabrication of the second plate-shaped member 3, the plate-shaped member 3a as a material of the second plate-shaped member 3 is prepared. Then as in FIG. 4A, while one end of the plate-shaped member 3a is supported at a support base 41, another end of the plate-shaped member 3a is supported at a driving element 42. The driving element 42 is loaded on the support base 41 and lifts up the other end of a main surface of the plate-shaped member 3a. As a result, the plate-shaped member 3a is placed still while angled at a fixed inclination angle θ. Then as illustrated in FIG. 4B, a tool 43 is moved horizontally to the inclined plate-shaped member 3a to cut the plate-shaped member 3a. As a result, the second plate-shaped member 3 is fabricated which has the inclined surface 5a angled at the fixed inclination angle θ.

The fabricated second plate-shaped member 3 is fixed to a plate-shaped member serving as the first plate-shaped member 2 through, for example, bonding. As a result, the device 1 having the wedge-shaped gap 6 is completed. For example, when a cutting depth is set at 10 nm, the height h2 of the opening in the other end 6b of the gap 6 (the outlet of the flow channel) is 10 nm. The height h1 of the opening in the one end 6a of the gap 6 (the inlet of the flow channel) is defined by a length L2 and the inclination angle θ of the plate-shaped member 3a.

Upon the fabrication of the second plate-shaped member 3, a step having a height that has already been adjusted is prepared and the plate-shaped member 3a is shaved linearly with the tool 43. This can cause the inclined surface 5a of the groove 5 to angle at the fixed inclination angle θ. For example, a piezoelectric element which is finely adjustable on the order of nanometers may be used for the driving element 42. For example, a blade of a precision processing machine finely adjustable on the order of nanometers may be used for the tool 43. For example, while angled at the fixed inclination angle θ by a piezoelectric element, the plate-shaped member 3a is placed still on a stage of a precision processing machine, and the stage and a blade of the precision processing machine are positioned in a manner such that the blade straightforwardly contacts the plate-shaped member 3a. Then a groove is dug linearly at the plate-shaped member 3a with the blade to fabricate the second plate-shaped member 3.

A bonding agent may be used for the bonding of the second plate-shaped member 3 to the first plate-shaped member 2. Alternatively, in a case where the first plate-shaped member 2 and the second plate-shaped member 3 are formed of resin such as acrylic resin, the first plate-shaped member 2 and the second plate-shaped member 3 may be thermally compressed (welded) by heating while superposed on each other.

Through the above, the method for producing the device 1 according to the first embodiment has been described. With the production method, the inclination angle θ of the plate-shaped member 3a having the predetermined length L2 can be controlled, thus permitting control of the inclination angle θ of the inclined surface 5a, that is, an angle of the wedge-shaped gap 6.

The use of, for example, the piezoelectric element, which is finely adjustable on the order of nanometers, as the driving element 42 makes it possible to control depth of the groove 5 (height of the gap 6) on the order of nanometers. This makes it possible to target particulates of a particle size on the order of nanometers (for example, several tens of nanometers or several hundreds of nanometers) for, for example, particle size measurement.

Note that the second plate-shaped member 3 may be fabricated by a mold. A portion of an inner surface of the clamped mold corresponding to the surface of the second plate-shaped member 3 on which the groove 5 is formed has a protrusion corresponding to the groove 5. For example, resin is filled in the mold to produce the second plate-shaped member 3. The fabrication of the second plate-shaped member 3 by using the mold makes it easy to mass-produce the devices 1.

In addition, the method for producing the device 1 may include a process of cleaning surfaces forming the gap 6 (surfaces forming the flow channel). For example, the surfaces forming the gap 6 are cleaned by a liquid such as ultrapure water. Alternatively, gas such as nitrogen gas is sprayed to the surfaces forming the gap 6. Alternatively, any foreign substance adhering to any of the surfaces forming the gap 6 is electrostatically removed. The cleaning may be carried out for each of the first plate-shaped member 2 and the second plate-shaped member 3 at a stage prior to the fixation of the second plate-shaped member 3 to the first plate-shaped member 2. Alternatively, the cleaning may be carried out after the fixation of the second plate-shaped member 3 to the first plate-shaped member 2. Note that the cleaning of the surfaces forming the gap 6 with the ultrapure water permits uniform absorption of water molecules to the surfaces forming the gap 6 to uniformize composition of the surfaces forming the gap 6. Therefore, the cleaning of the surfaces forming the gap 6 with the ultrapure water permits the cleaning of the surfaces forming the gap 6 and also the uniformization of the composition of the surfaces forming the gap 6.

The method for producing the device 1 may include a process of uniformizing the composition of the surfaces forming the gap 6. For example, ultraviolet rays are irradiated to the surfaces forming the gap 6. Alternatively, the surfaces forming the gap 6 are dried through heating. The process of uniformizing the composition of the surfaces forming the gap 6 may be carried out for each of the first plate-shaped member 2 and the second plate-shaped member 3 at the stage prior to the fixation of the second plate-shaped member 3 to the first plate-shaped member 2. Alternatively, the process of uniformizing the composition of the surfaces forming the gap 6 may be carried out after the fixation of the second plate-shaped member 3 to the first plate-shaped member 2. Note that, in a case where the surfaces forming the gap 6 are formed of glass, the surfaces forming the gap 6 may be activated (reformed) through heat application to the surfaces forming the gap 6.

The method for producing the device 1 may include a process of reforming the surfaces forming the gap 6. For example, ultraviolet rays are irradiated to the surfaces forming the gap 6 to activate the surface forming the gap 6. Alternatively, in a case where a material of the surfaces forming the gap 6 is a hydrophilic material such as untreated glass and particles are hardly blended in water, a medicinal agent such as a surfactant may be used to make the surfaces forming the gap 6 hydrophobic. Making the surfaces forming the gap 6 hydrophobic makes it easy for the particles to enter into the gap 6 (flow channel). The process of reforming the surfaces forming the gap 6 may be carried out for each of the first plate-shaped member 2 and the second plate-shaped member 3 at the stage prior to the fixation of the second plate-shaped member 3 to the first plate-shaped member 2. Alternatively, the process of reforming the surfaces forming the gap 6 may be carried out after the fixation of the second plate-shaped member 3 to the first plate-shaped member 2. Note that ultraviolet rays is irradiated to the surfaces forming the gap 6 to decompose a foreign substance such as an organic substance adhering to the surfaces forming the gap 6. Therefore, the ultraviolet ray irradiation to the surfaces forming the gap 6 before the cleaning of the surfaces forming the gap 6 makes it easy to remove the foreign substance, such as the organic substance, from the surfaces forming the gap 6.

In a case where the surfaces forming the gap 6 are formed of resin, the method for producing the device 1 may include a process of glass-coating the surfaces forming the gap 6. The aforementioned cleaning process, uniformization process, and reforming process are carried out after the glass-coating of the surfaces forming the gap 6.

Next, one example of a method for measuring particle sizes of particulates by using the device 1 will be described with reference to FIGS. 5A to 5D and 6 to 8. FIGS. 5A to 5D and 6 schematically illustrate the particle size measurement method according to the first embodiment of the present invention. The particle size measurement method is executed by: a process of preparing the device 1, a process of preparing a solution 50 including particulates 51 and a solvent 52; a process of injecting the solution 50; and a process of measuring the particle sizes.

In the process of preparing the device 1, the device 1 described with reference to FIGS. 1 to 3 is prepared.

Figure 5A:
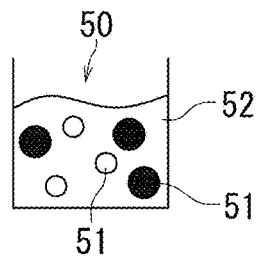
FIG. 5A is a schematic view illustrating a solution preparation process according to the first embodiment of the present invention.

FIG. 5A is a schematic view illustrating a solution preparation process of preparing the solution 50. As illustrated in FIG. 5A, the solution 50 including the particulates 51 and the solvent 52 is prepared in the process. More specifically, the solvent 52 and the particulates 51 as a measurement target are prepared, and the particulates 51 are added to the solvent 52 to make the solution 50. To obtain an accurate particle sizes, the particulates 51 are preferably dispersed in the solvent 52 in a uniform manner.

In the first embodiment, two types of a plurality of particulates 51 of different particle sizes are prepared, but the present invention is not limited thereto. The number of types of the particulates 51 may be one or more, and one or more particles of each type may be prepared. The particulates 51 are, for example, high molecules, metal, non-metal, or biological body particulates (for example, cells, vesicles such as exosome, DNA, protein, or virus). However, the present invention is not limited thereto. Any particulate 51 that can be transported into the gap 6 of the device 1 via a medium such as a liquid or gas can be applied as a measurement target. To deliver the particulates 51 into the gap 6 by using gas, for example, gas including the particulates 51 is sprayed to an inside of the gap 6 from the opening in the one end 6a of the gap 6 (the inlet of the flow channel) to trap the particulates 51 in the gap 6. Alternatively, after the delivery of the particulates 51 into the gap 6 by using the gas, impact is added on the device 1 with the other end 6b of the gap 6 oriented downward to move the particulates 51 for trapping the particulates 51 in the gap 6.

The solvent 52 may be, for example, water or an organic solvent (for example, ethanol or benzene). However, the present invention is not limited thereto. It is possible to appropriately select the solvent 52 in accordance with the particulates 51 to be measured.

Figure 5B:
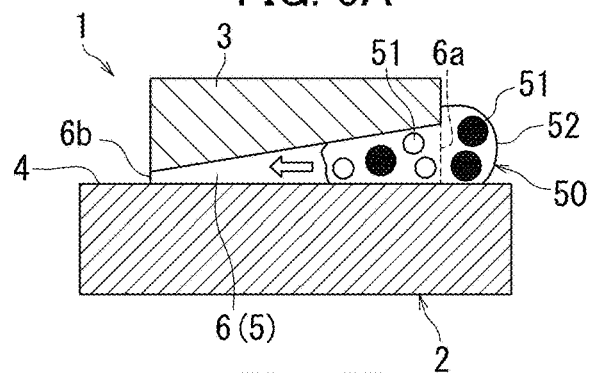
FIG. 5B is a cross-sectional view schematically illustrating a solution injection process according to the first embodiment of the present invention.

FIG. 5B is a cross-sectional view schematically illustrating the solution injection process of injecting the solution 50. As illustrated in FIG. 5B, the solution 50 is injected into the gap 6 of the device 1 in the process. More specifically, the solution 50 can be made flow from the opening in the one end 6a of the gap 6 (the inlet of the flow channel) into the gap 6 (flow channel) through dropping the solution 50 onto the solution introduction part 7 of the first plate-shaped member 2.

Figure 5C:
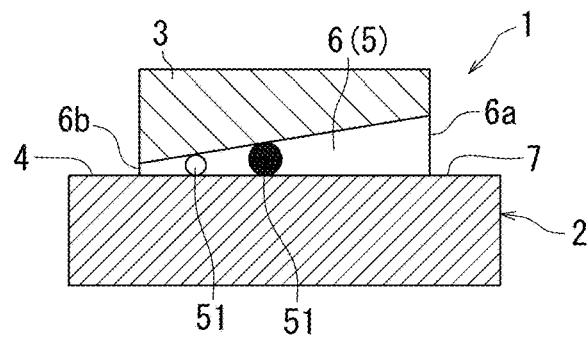
FIG. 5C is a cross-sectional view schematically illustrating particulates trapped by the device according to the first embodiment of the present invention.
Figure 5D:
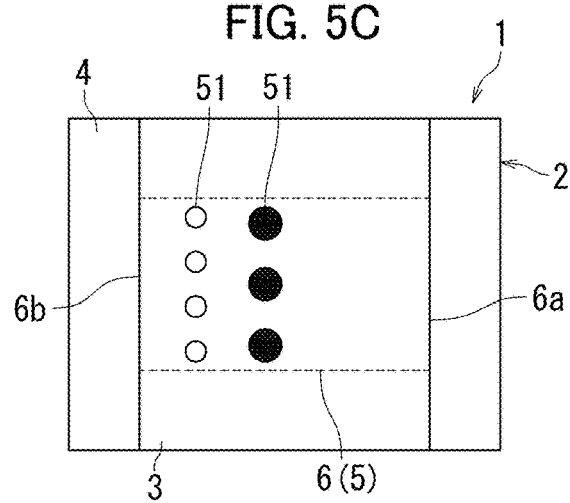
FIG. 5D is a top view schematically illustrating particulates trapped by the device according to the first embodiment of the present invention.

FIG. 5C is a cross-sectional view schematically illustrating the trapped particulates 51, and FIG. 5D is a top view schematically illustrating the trapped particulates 51. Upon the flow of the solution 50 into the gap 6 (flow channel), the particulates 51 included in the solution 50 move toward the other end 6b of the gap 6 (the outlet of the flow channel). Then as illustrated in FIGS. 5C and 5D, the particulates 51 are trapped at portions of the gap 6 in accordance with sizes of the respective particulates 51. More specifically upon the dropping of the solution 50 to the solution introduction part 7 of the first plate-shaped member 2 in the solution injection process, the solvent 52 is sucked toward the other end 6b of the gap 6 (the outlet of the flow channel) through a capillary action of the gap 6. Then by using, as the driving force, the force by which the solvent 52 is sucked, the particulates 51 included in the solution 50 move toward the other end 6b of the gap 6 (the outlet of the flow channel), and the particulates 51 are trapped at the portions of the gap 6 in accordance with the sizes of the respective particulates 51.

Figure 6:
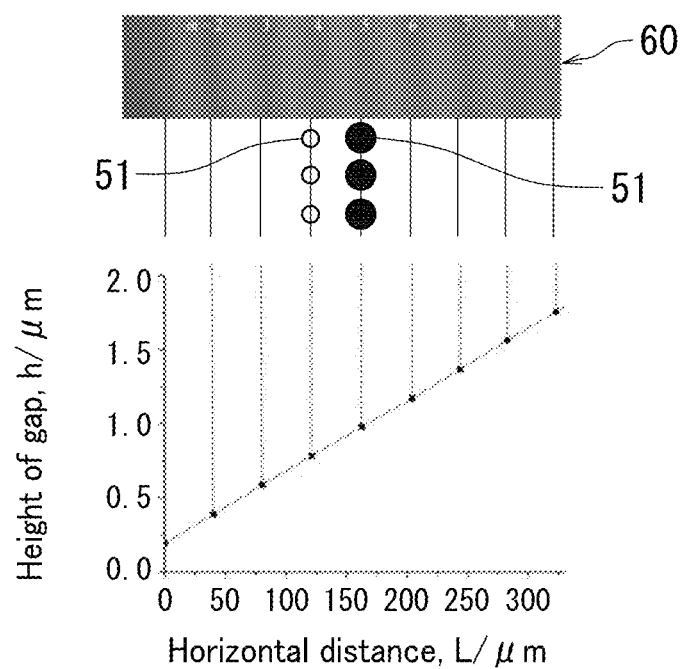
FIG. 6 is a schematic view illustrating a particle size measurement process according to the first embodiment of the present invention.

FIG. 6 is a schematic view illustrating the measurement process of measuring the particle sizes of the particulates 51. In the measurement process, the particle sizes of the trapped particulates 51 are measured based on an interference fringe 60 caused to appear by the gap 6 as illustrated in FIG. 6. More specifically describing, in the measurement process, the particle size of each of the particulates 51 is measured based on relationship between the height h of the gap 6 and distance (horizontal distance) L from the other end 6b of the gap 6 and based on each position where each of the particulates 51 is trapped.

Figure 7:
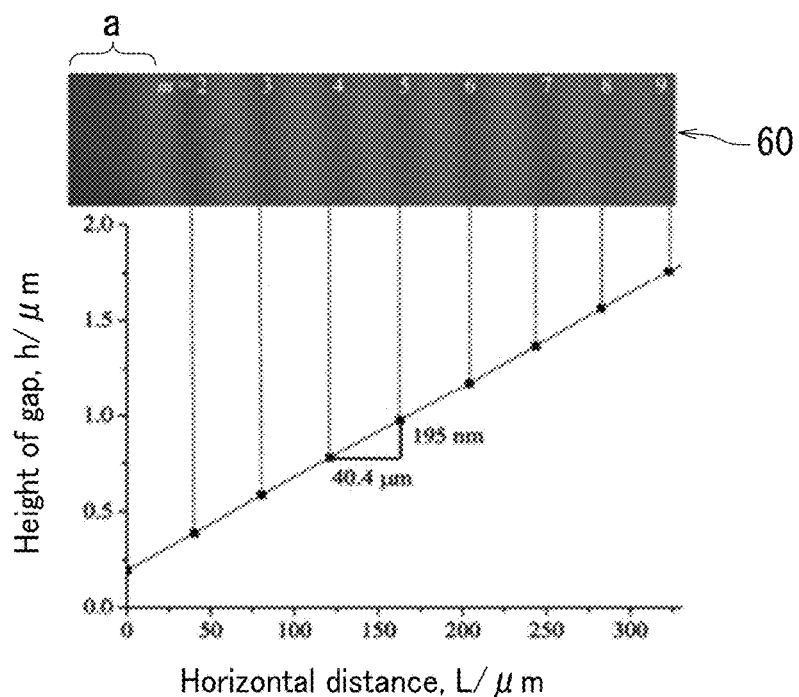
FIG. 7 is a schematic view illustrating principles of a particle size measurement method according to the first embodiment of the present invention.
Figure 8:
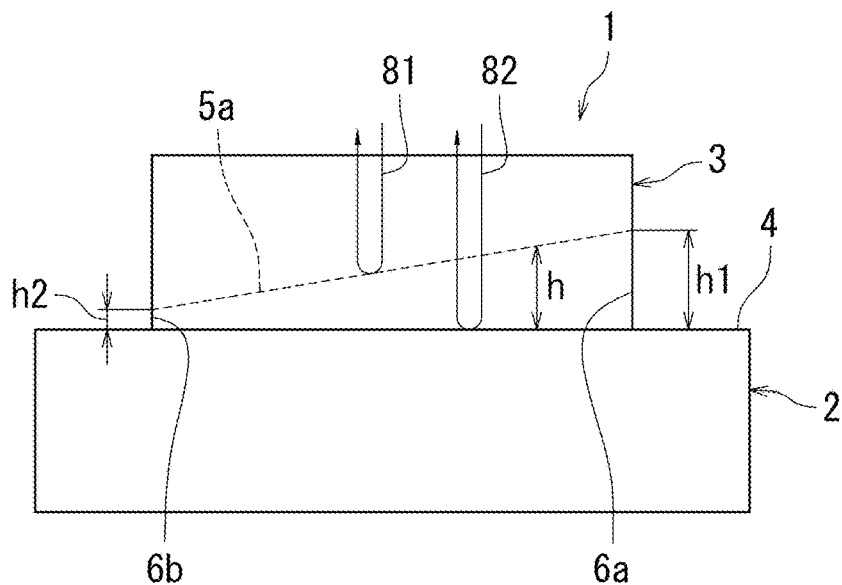
FIG. 8 is a side view schematically illustrating reflection of a light beam irradiated to the device according to the first embodiment of the present invention.

FIG. 7 is a schematic view illustrating principles of the particle size measurement method, and FIG. 8 is a side view schematically illustrating reflection of a light beam irradiated to the device 1. Due to the presence of the wedge-shaped gap 6 between the first plate-shaped member 2 and the second plate-shaped member 3, irradiation of a light beam of a single wavelength to the device 1 causes an interference fringe 60 repeatedly having a bright line and a dark line to appear, as illustrated in FIG. 7. The appearance is caused due to, as illustrated in FIG. 8, a difference in an optical path length between a returning light beam 81 reflected on the inclined surface 5a of the second plate-shaped member 3 and a returning light beam 82 reflected on the main surface 4 of the first plate-shaped member 2 in a situation in which the inclined surface 5a of the second plate-shaped member 3 is located in close proximity to the main surface 4 of the first plate-shaped member 2. Further, since the gap 6 has the wedge shape that becomes continuously narrower, the interference fringe 60 is formed in a manner such that both of bright lines and dark lines are located at equal intervals. The intervals between the bright lines and the intervals between the dark lines are determined depending on the wavelength of the light beam. Relationship between the observed bright lines and dark lines is expressed by formulae below.

$$\text{Dark Line Condition: } h = m(\lambda/2n) \quad (1)$$

$$\text{Bright Line Condition: } 2h = (\lambda/2n)(2m+1) \quad (2)$$

In the formulae (1) and (2), h represents the height of the gap 6 and m represents an integer number (m=0, 1, 2, 3 . . . ). Symbol $\lambda$ represents the wavelength of the light beam of the single wavelength and n represents a refractive index of a medium filled inside of the gap 6 upon the appearance of the interference fringe 60. For example, in a case where the inside of the gap 6 is filled with water, n is 1.333.

In the particle size measurement method according to the first embodiment, the particle sizes of the particulates 51 are measured based on the dark lines. In a case where the wavelength $\lambda$ and the refractive index n are already known, according to the formula (1), the height h of the gap 6 at a position where the m-th dark line has appeared can be calculated. Therefore, observation of the number of dark lines in the interference fringe 60 provides a relational expression (direct function) between the height h of the gap 6 and the distance (horizontal distance) L from the other end 6b of the gap 6. Thus, by observing the particulates 51 in the gap 6 to obtain the positions where the particulates 51 are trapped, the heights h of the gap 6 at the positions where the particulates 51 are trapped can be calculated as the particle sizes of the particulates 51 based on the relational expression between the height h of the gap 6 and the horizontal distance L and based on the positions of the particulates 51 obtained through the observation. Note that the process of causing the interference fringe 60 to appear and obtaining the relational expression between the height h of the gap 6 and the horizontal distance L may be executed before or after the delivery of the particulates 51.

Through the above, the particle size measurement method according to the first embodiment has been described. In the particle size measurement method, the height h of the wedge-shaped space (gap 6) inside of the device 1 is measured to obtain the particle size of each of the particulates 51. More specifically, the number of dark lines of the interference fringe 60 is observed to obtain the relational expression (direct function) between the height h of the gap 6 and the horizontal distance L. Then based on the relational expression, the heights h of the gap 6 at the positions where the particulates 51 have stopped are calculated as the particle sizes of the particulates 51. With the device 1, particle size measurement of the particulates 51 of particle sizes within a range between approximately 10 nm and 100 µm can be made. In a case where the particle sizes 51 have a long axis and a short axis, the particulates 51 are trapped at the short axis that is less resistant in a fluid. Therefore, the particle sizes to be measured are sizes of the short axes of the particulates 51 in this case. Use of a plurality of types of devices 1 that differ in at least one of the angle $\theta$ and the length L1 permits various particulates 51 of mutually different particle sizes to be targeted for the particle size measurement.

According to the first embodiment, it is possible to set the angle $\theta$ of the wedge-shaped gap 6, which hardly results in variation in the height h of the gap 6 between the plurality of devices 1. Therefore, variation in the devices 1 between different product lots can be suppressed. For example, with a particle size measurement device including two glass plates one of which is obliquely superposed on another, it is difficult to set an angle between the two glass plates, that is, an angle of a wedge-shaped gap, which is likely to result in great variation between the plurality of devices in distance between the two glass plates (height of the wedge-shaped gap). This may cause variation in particle size measurement between the plurality of devices. On the contrary, according to the first embodiment, it is possible to set the angle of the wedge-shaped gap 6. Therefore, variation in the particle size measurement hardly occurs between the plurality of devices. Note that it is possible to widen a range of the particle size measurement in a smaller region with an increase in the angle $\theta$ of the gap 6. On the other hand, particle separability is further improved with a decrease in the angle $\theta$ of the gap 6.

A dynamic light scattering method, a microscopic observation method, etc. have been known as typical particle size measurement methods, but with the particle size measurement methods other than the microscopic observation method, only the number of particulates can statistically be estimated, while it is difficult to count the statistically significant number of particulates with the microscopic observation method. On the contrary, according to the first embodiment, it is possible to easily count the number of particulates 51 conveyed into the gap 6. For example, it is of diagnostic significance to accurately count the number of cells in a clinical test. The device 1 is useful in a field where it is required to accurately count the number of particulates, for example, in a clinical test.

Figure 9:
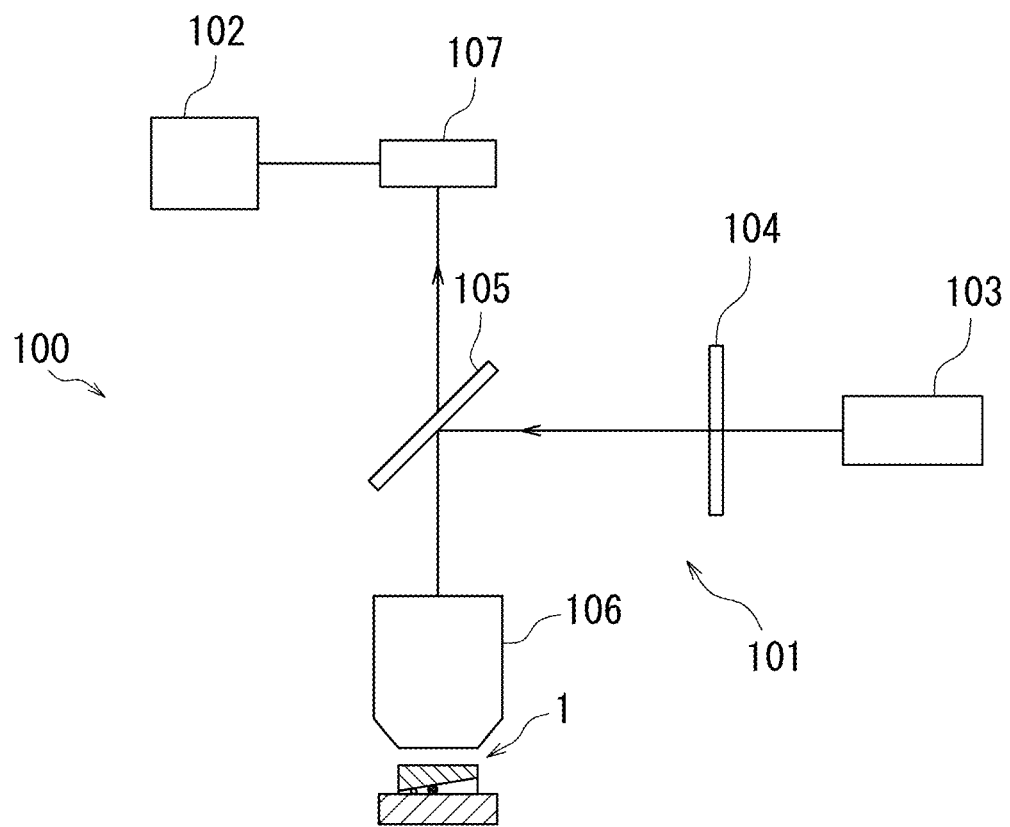
FIG. 9 is a schematic view illustrating configuration of a particle size measurement apparatus according to the first embodiment of the present invention.

Next, one example of configuration of an apparatus that measures a particle size will be described with reference to FIG. 9. FIG. 9 is a schematic view illustrating configuration of a particle size measurement apparatus 100 (one example of an observation apparatus) according to the first embodiment of the present invention. The particle size measurement apparatus 100 includes an observing optical system 101 and an analysis section 102.

The observing optical system 101 includes: a light source 103, a filter 104, a mirror 105, an objective lens 106, and a camera 107. The light source 103 generates a light beam for causing the interference fringe 60 to appear in the device 1 as illustrated in FIGS. 6 and 7. The light source 103 may generate a light beam of a single wavelength or may generate a light beam of a non-single wavelength. The light source 103 is preferably a laser generator that generates a light beam of a single wavelength.

A light beam generated from the light source 103 is converted into a light beam of a single wavelength by the filter 104. In a case where the light source 103 generates a light beam of a single wavelength, the filter 104 may be omitted. The light beam converted into the light beam of the single wavelength is reflected on the mirror 105, and irradiated to the device 1 through the objective lens 106. Then the light beam reflected from the device 1 passes through the objective lens 106 and the mirror 105, and is recorded as an image by the camera 107.

The analysis section 102 analyzes the particle sizes of the particulates 51 based on results of observation performed in the observing optical system 101. For example, the analysis section 102 is a computer that analyzes the image recorded by the camera 107. With the computer, necessary information such as the number of dark lines of the interference fringe 60 and the positions where the particulates 51 are trapped can be analyzed from the image to calculate the particle sizes of the particulates 51. Moreover, the number of particulates 51 in the gap 6 can be counted.

Note that the analysis section 102 may have a function of analyzing the image recorded by the camera 107 to obtain information on a direction perpendicular to a height direction of the particulate 51 (two-dimensional information such as particle area of the particulate 51). Since the information on the height direction of the particulate 51 (circle equivalent diameter or one-dimensional size of the particulate 51), can be obtained through image analysis by the analysis section 102, shape of the particulate 51 can be evaluated by obtaining the two-dimensional information. Specifically, through the image analysis, the information on the height direction of the particulate 51 (particle size) and the two-dimensional information (for example, particle area) of the particulate 51 are obtained. Then the shape of the particulate 51 is evaluated based on the information on the height direction and the two-dimensional information. This makes it possible to measure degrees of sphericity (sphericity) of the particulates 51, measure particle size distribution on an individual shape basis, and detect agglomerates.

Figure 10:
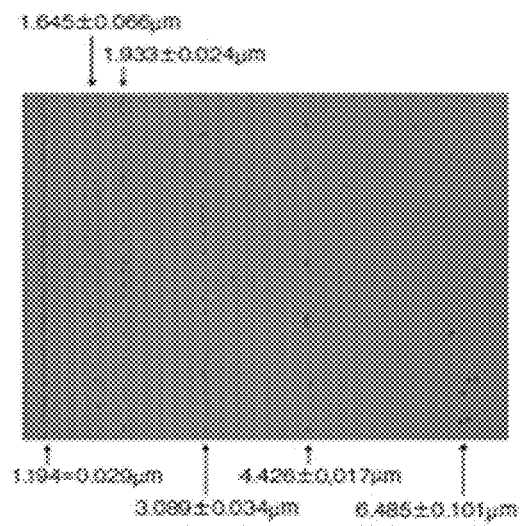
FIG. 10 shows a photograph in place of a drawing illustrating results of trapping standard polystyrene particles by the device according to the first embodiment of the present invention.

As described above, in the device 1, the particulate 51 can be trapped at the position in accordance with the particle size of the particulate 51 in the wedge-shaped gap 6 (the flow channel). Then accurate particle sizes can be measured based on the interference fringe 60. Particle sizes of standard polystyrene particles were measured as one example. The standard polystyrene particles are polystyrene particles having known particle sizes. FIG. 10 shows a photographed image. Table 1 shows measurement results. A left column in Table 1 represents standard values of the particle sizes of the standard polystyrene particles as measurement targets, and a right column in Table 1 represents measured values. As a result of the measurement, the standard values of the particle sizes and the measured values of the particle sizes were close to each other.

TABLE 1

| Standard polystyrene particles Standard values/μm | Measured values/μm |
| --- | --- |
| 1.019 ± 0.018 | 1.194 ± 0.029 |
| 1.614 ± 0.064 | 1.645 ± 0.066 |
| 2.092 ± 0.095 | 1.933 ± 0.024 |
| 3.004 ± 0.065 | 3.089 ± 0.034 |
| 4.518 ± 0.152 | 4.426 ± 0.017 |
| 6.217 ± 0.125 | 6.485 ± 0.101 |

Figure 11:
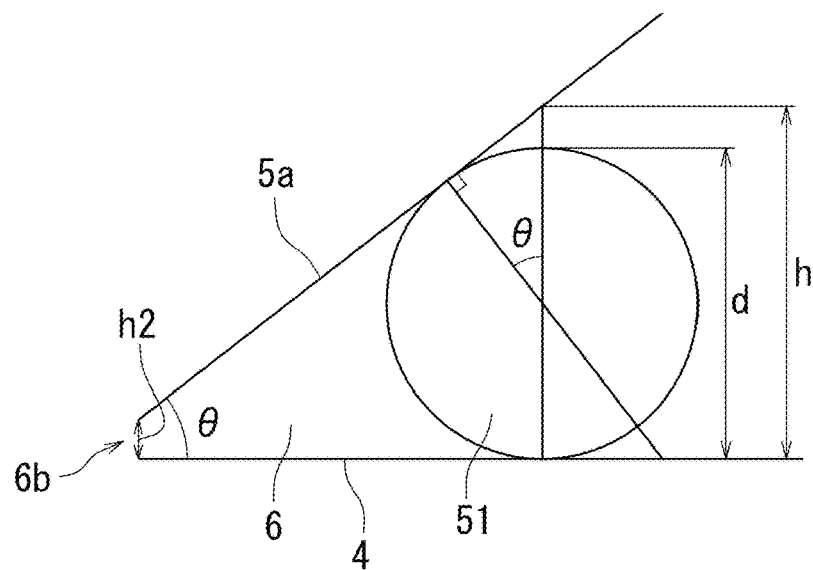
FIG. 11 is a schematic view illustrating principles of a particle size correction method according to the first embodiment of the present invention.

Next, a particle size correction method will be described with reference to FIG. 11. FIG. 11 is a schematic view illustrating principles of the particle size correction method according to the first embodiment of the present invention. In the particle size measurement method described above, the height h of the gap 6 at the position where the particulate 51 is trapped was obtained as the particle size of the particulate 51. However, the height h of the gap 6 at the position where the particulate 51 is trapped is slightly larger than an actual diameter d of the particulate 51, as illustrated in FIG. 11. Thus, correction is required to obtain the diameter d of the particulate 51. The diameter d of the particulate 51 is expressed by a formula below.

$$d = 2h/((1/\cos \theta) + 1) \quad (3)$$

In the formula (3), $\theta$ represents an angle of the wedge-shaped gap 6 (the inclination angle $\theta$ of the inclined surface 5a), and is calculated by a formula below by using a distance $\Delta L$ between the adjacent dark lines of the interference fringe 60.

$$\tan \theta = \lambda/(2n\Delta L) \quad (4)$$

The distance $\Delta L$ between the adjacent dark lines of the interference fringe 60 is obtained by analyzing the image of the interference fringe 60. Through formulae (3) and (4), relationship between the diameter d of the particulate 51 and the height h of the gap 6 can be corrected by a formula below.

$$d = 2((1/\Delta L)(\lambda/2n)L + h2)/((1/\cos \theta) + 1) \quad (5)$$

In the formula (5), $\lambda$ represents a wavelength of a light beam causing the interference fringe 60 to appear, n represents a refractive index of the medium filled inside of the gap 6 upon the appearance of the interference fringe 60, L represents the position (horizontal distance) where the particulate 51 is trapped, $\Delta L$ represents the distance between the adjacent dark lines of the interference fringe 60, $\theta$ represents the angle of the wedge-shaped gap 6 (the inclination angle of the inclined surface 5a), and h2 represents a minimum height of the gap 6, that is, an opening height of the other end 6b of the gap 6.

According to the formula (5), parameters required for calculating the diameter d include the wavelength $\lambda$, the refractive index n, the horizontal distance L, the distance $\Delta L$ between the adjacent dark lines, the minimum height h2 of the gap 6, and the inclination angle θ of the inclined surface 5a. Of these parameters, the wavelength λ and the refractive index n are well-known, and thus the diameter d can be obtained by the formula (5) by obtaining the horizontal distance L, the distance ΔL between the adjacent dark lines, and the minimum height h2 of the gap 6. Note that the inclination angle θ of the inclined surface 5a can be obtained by the formula (4). Moreover, the minimum height h2 of the gap 6 can be obtained from the relational expression (direct function) between the height h of the gap 6 and the horizontal distance L.

In case of particle size measurement performed by using the particle size measurement apparatus 100 described with reference to FIG. 9, the horizontal distance L, the distance ΔL between the adjacent dark lines, and the minimum height h2 of the gap 6 can be obtained through analysis by the analysis section 102 on an image recorded with the camera 107 to calculate the diameter d.

Note that the inclination angle θ of the inclined surface 5a and the minimum height h2 of the gap 6 may be obtained based on the angle at which the plate-shaped member 3a has been inclined upon the fabrication of the second plate-shaped member 3 and based on the cutting depth. Note that the angle at which the plate-shaped member 3a has been inclined and the cutting depth are influenced by positional accuracy of the support base 41, driving accuracy of the driving element 42, abrasion of the tool 43 as a result of the cutting, etc. For example, in a case where a piezoelectric element is used as the driving element 42, driving accuracy of the piezoelectric element depends on a voltage and is thus influenced by accuracy of a power source. Therefore, even in a case where the angle at which the plate-shaped member 3a has been inclined and the cutting depth are used as the parameters, the parameters are desirably corrected by using the interference fringe 60.

The device 1 is disposable since the device 1 has simple configuration, are easy to produce, and has low unit costs. Based on the above, the device 1 is preferable for particle size measurement under environment (for example, in a clinical test) where recycling is not preferable. Moreover, in the particle size measurement method using the device 1, the particle size can be calculated through observation of the interference fringe 60 and the particulate 51 without using complicated analysis formula or correction formula. Thus measurement results that are easily and highly reproducible can be obtained.

With the device 1, the particulates 51 can be trapped in the gap 6 for the particle size measurement, but use application of the device 1 is not limited thereto. The device 1 can also be used for other purposes, for example, observing the particulates 51 after the trapping of the particulates 51 into the gap 6 or making a predetermined reaction liquid flow into the gap 6 to cause reaction of the particulates 51 thereto. For example, in a case where the device 1 is used for the purpose of causing reaction between the particulates 51 with a modified antigen and a predetermined reaction liquid, after the particulates 51 with the modified antigen are trapped into the gap 6, a solution containing an antibody is made flow into the gap 6 to cause reaction of only the particulates 51 with the antigen. Hereinafter, examples in which the device 1 is used for the other purposes will be described.

The device 1 can be used for the purpose of observing resistance of the particulates 51. More specifically, particulates 51, which are delivered from the opening in the one end 6a of the gap 6 into the gap 6 of the device 1, are moved toward the other end 6b of the gap 6 to be trapped in the gap 6. Subsequently, physical stress such as light or heat is added to the trapped particulates 51. This permits verification of the resistance of the particulates 51 against the physical stress.

Alternatively, after the trapping of the particulates 51, a predetermined reactive fluid is injected from the opening in the one end 6a of the gap 6. The reactive fluid is, for example, a reaction liquid or reactive gas. This permits verification of resistance of the particulates 51 against the predetermined reactive fluid. Note that before introduction of the predetermined reactive fluid, the inside of the gap 6 is preferably dried.

Figures 12A, 12B, 12C:
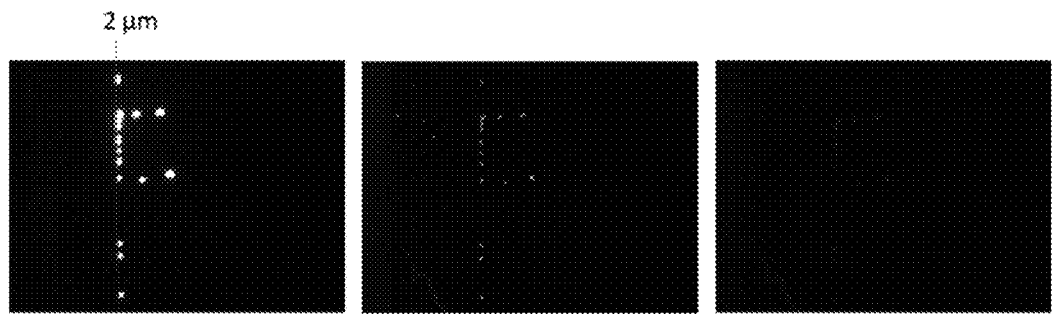
FIGS. 12A to 12C show photographs in place of drawings illustrating results of testing resistance of standard polystyrene particles against tetrahydrofuran by using the device according to the first embodiment of the present invention.

Resistance of standard polystyrene particles against tetrahydrofuran was tested as one example. In the test, after the standard polystyrene particles were trapped in the gap 6, the inside of the gap 6 was dried. Subsequently, after a 50% tetrahydrofuran aqueous solution (a corrosion solution) was introduced into the gap 6, the inlet and outlet of the gap 6 (the opening in the one end 6a of the gap 6 and the opening in the other end 6b of the gap 6) were covered, and how the standard polystyrene particles are corroded was observed. FIGS. 12A to 12C show photographed images.

FIG. 12A shows the image photographed before the introduction of the 50% tetrahydrofuran aqueous solution into the gap 6. FIG. 12B shows the image photographed two minutes after the introduction of the 50% tetrahydrofuran aqueous solution into the gap 6. FIG. 12C shows the image photographed ten minutes after the introduction of the 50% tetrahydrofuran aqueous solution into the gap 6. It is found from FIGS. 12A to 12C that the polystyrene particles are dissolved by the tetrahydrofuran aqueous solution. That is, it is found that the polystyrene particles have no resistance against the tetrahydrofuran aqueous solution.

As described above, through the introduction of the predetermined reactive fluid into the gap 6 where the particulates 51 have been trapped, it can be recognized whether or not the particulates 51 have resistance against the predetermined reactive fluid. Specifically, in a case where the particulates 51 have resistance against the predetermined reactive fluid, the particulates 51 remain intact in the gap 6 even after the introduction of the predetermined reactive fluid into the gap 6. On the other hand, in a case where the particulates 51 have no resistance against the predetermined reactive fluid, the particulates 51 disappear or are at least downsized in the gap 6 after the introduction of the predetermined reactive fluid into the gap 6. Alternatively, in a case where the positions where the particulates 51 are trapped are changed due to downsizing of the particulates 51, the resistance of the particulates 51 can also be verified based on the change.

Note that a resistance test of the particulates 51 may be performed after the particle size measurement. On the other hand, in a case where the device 1 is used only for verifying the resistance of the particulates 51, the particulates 51 may not be trapped in the gap 6. For example, the particulates 51 may be absorbed to the surfaces forming the gap 6.

The particulates 51 in the gap 6 can be observed on a microscope. Alternatively, the particulates in the gap 6 may be photographed by the observing optical system including the objective lens and the camera.

The device 1 can also be used for the purpose of causing chemical reaction of the particulates 51. More specifically, the particulates 51, which are delivered from the opening in the one end 6a of the gap 6 into the gap 6 of the device 1, are moved toward the other end 6b of the gap 6 to be trapped in the gap 6. Subsequently, a predetermined reactive fluid is injected from the opening in the one end 6a of the gap 6. The reactive fluid is, for example, a reaction liquid or reactive gas. As a result, chemical reaction of the particulates 51 to the predetermined reactive fluid can be verified. Note that the inside of the gap 6 is preferably dried before the introduction of the predetermined reactive fluid.

Through the above, the chemical reaction method using the device 1 has been described. The chemical reaction method is applicable to various purposes for observing reaction between the particulates 51 and any predetermined reactive fluid, for example, observing a change in particle size distribution as a result of causing reaction of the particulates 51 to the predetermined reactive fluid. Further, the introduction of the predetermined reactive fluid into the gap 6 where the particulates 51 are trapped makes it possible to subject the particulates 51 to chemical modification. Moreover, the introduction of the predetermined reactive fluid into the gap 6 where the particulates 51 are trapped also permits staining of the particulates 51. Therefore, a specific one type of the particulates 51 trapped in the gap 6 can be detected.

Therefore, with the chemical reaction method, information useful for quality control of particulates can be obtained. Further, observation of a change in each of the particulates also permits evaluation of composition uniformity of the particulates 51. Note that treatment of causing chemical reaction of the particulates 51 may be performed after the particle size measurement. On the other hand, in a case where the device 1 is used only for causing chemical reaction of the particulates 51, the particulates 51 may not be trapped in the gap 6. For example, the particulates 51 may be absorbed to the surfaces forming the gap 6.

Moreover, the device 1 can be used for preserving the particulates 51. More specifically, the particulates 51, which are delivered from the opening in the one end 6a of the gap 6 into the gap 6 of the device 1, are moved toward the other end 6b of the gap 6 to be trapped in the gap 6. Subsequently, for example, a bonding agent is applied to the inlet and outlet of the gap 6 (the opening in the one end 6a of the gap 6 and the opening in the other end 6b of the gap 6) to cover the inlet and outlet of the gap 6. This seals the gap 6, thereby permitting preservation of the particulates 51 trapped in the gap 6. Note that treatment of preserving the particulates 51 may be performed after the particle size measurement. On the other hand, in a case where the device 1 is used only for preserving the particulates 51, the particulates 51 may not be trapped in the gap 6. For example, the particulates 51 may be absorbed to the surfaces forming the gap 6.

Before closing the inlet and the outlet of the gap 6 of the device 1, a predetermined preservative fluid composed of a substance that is not reactive to the particulates 51 is preferably injected into the gap 6. The preservative fluid is, for example, a preservative solution or preserve gas. Filling the inside of the gap 6 with the substance not reactive to the particulates 51 and closing the inlet and outlet of the gap 6 with a material (for example, a bonding agent or a resin film) having no influence on the substance sealed into the gap 6 make it possible to achieve long-term preservation of the particulates 51. For example, to preserve the particulates 51 of a biological origin, formalin is introduced as an anticorruption agent into the gap 6.

Moreover, before closing the inlet and outlet of the gap 6 of the device 1, the inside of the gap 6 is preferably dried. Instead of applying the bonding agent, the resin film may be thermally compressed to the inlet and outlet of the gap 6 to seal the gap 6.

Figure 13:
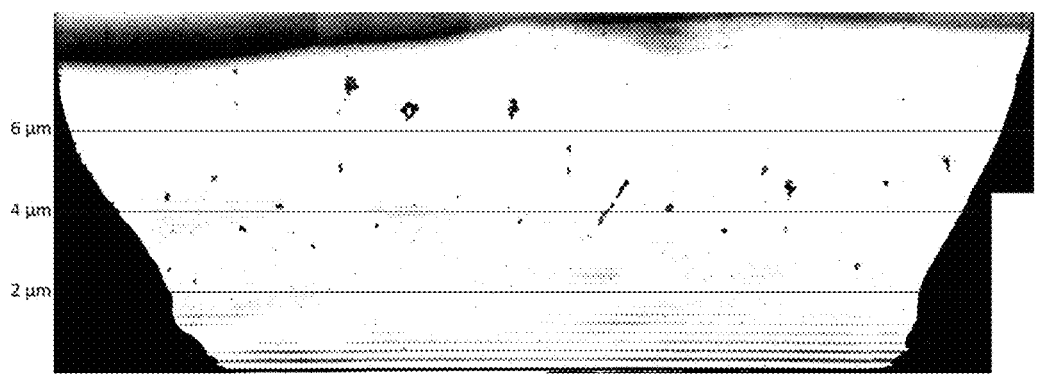
FIG. 13 shows a photograph in place of a drawing illustrating ink toner particles preserved by using the device according to the first embodiment of the present invention.

Ink toner particles were preserved as one example. FIG. 13 shows a photographed image of the ink toner particles preserved in the gap 6. More specifically, after the ink toner particles were trapped, the inside of the gap 6 of the device 1 was dried. Subsequently, the inlet and outlet of the gap 6 (the opening in the one end 6a of the gap 6 and the opening in the other end 6b of the gap 6) were closed by a resin to adjust the gap 6 suitably for the preservation of the ink toner particles.

Through the above, the method for preserving the particulates 51 by using the device 1 has been described. With the preservation method, for example, retaining the device 1 after the particle size measurement of the particulates 51 can make a contribution to quality control of the particulates 51. Therefore, lot-control on a vendor's side can easily be performed. For example, a vendor of an ink toner is required to retain ink toner particle samples for long time for the purpose of quality control. Use of the device 1 permits preservation of the ink toner particles remaining trapped in the device 1 after the particle size measurement thereof. That is, the particle samples can be retained while environment in which the particle size measurement is performed is maintained. Therefore, it is useful for ink lot control. Moreover, time and costs required for performing the particle size measurement again can be reduced.

The device 1 can also be used for selection (screening) of the particulates 51 in accordance with particle sizes. More specifically, the particulates 51, which are delivered from the opening in the one end 6a of the gap 6 into the gap 6 of the device 1, are moved toward the other end 6b of the gap 6. This permits the particulates 51 of a particle size smaller than the height h2 of the opening in the other end 6b of the gap 6 (the outlet of the flow channel) to be delivered from the opening in the other end 6b of the gap 6 to an outside of the gap 6. On the other hand, the particulates 51 of a particle size larger than the height h2 of the opening in the other end 6b of the gap 6 remains inside of the gap 6. Therefore, the device 1 can be used to perform the selection of the particulates 51 in accordance with particle sizes thereof.

For example, to select and take out the particulates 51 of a particle size smaller than a predetermined value from a solution in which a plurality of types of particulates 51 of mutually different particle sizes are mixed, a device 1 in which the height h2 of the opening in the other end 6b of the gap 6 is equal to the predetermined value is used. As a result, only the particulates 51 of the particle size smaller than the predetermined value are delivered from the opening in the other end 6b of the gap 6 to the outside of the gap 6. Therefore, the particulates 51 of the particle size smaller than the predetermined value can be selected and taken out.

Through use of the device 1, it is also possible to deliver even smaller particulates included in the particulates 51 from the opening in the other end 6b of the gap 6 to the outside of the gap 6 after the trapping of the particulates 51 in the gap 6. For example, exosomes, which are delivered from the opening in the one end 6a of the gap 6 into the gap 6 of the device 1, are moved toward the other end 6b of the gap 6 to be trapped in the gap 6. Then alcohol is made flow into the gap 6 from the opening in the one end 6a of the gap 6. As a result, the exosome is dissolved in the gap 6, so that a gene flows out of the exosome and the gene is delivered together with the alcohol from the opening in the other end 6b of the gap 6 to the outside of the gap 6. As described above, the use of the device 1 in this manner makes it possible to take the gene out of the exosome.

Through the above, the first embodiment has been described. According to the first embodiment, for example, it is possible to perform analysis of all the particulates 51 included in a sample solution. Therefore, particle size distribution of the particulates 51 can be measured. In a case where the sample solution is a high-concentration solution, the particulates 51 may be deposited in the gap 6. In this case, after a plurality of devices 1 are prepared and the sample solution is diluted, the diluted sample solution may be introduced to each device 1 by a small amount at a time. According to the first embodiment, it is also possible to analyze particulates as a measurement target without depending on colors of the particulates. For example, even when the particulates as the measurement targets are in black that absorbs light, the particulates can be analyzed. Therefore, it is possible to measure particle size distribution of the black ink toner. Thus, the device 1 is useful for analysis of an ink pigment.

In the first embodiment, the first plate-shaped member 2 has a longer length than the second plate-shaped member 3 in the direction in which the inclined surface 5a is inclined, and a portion of the main surface 4 of the first plate-shaped member 2 on an outer side of the one end 6a of the gap 6 is used as the solution introduction part 7. Note that, however, the device of the present invention is not limited to the aforementioned configuration. The first plate-shaped member 2 may be shorter than the second plate-shaped member 3 in the direction in which the inclined surface 5a is inclined. In this case, a part of the second plate-shaped member 3 serves as the solution introduction part 7.

In the first embodiment, the plate-shaped member is used as one example of the first member, but a shape of the first member is not limited to a plate shape. For example, the shape of the first member may be a rectangular parallelepiped. Similarly, a shape of the second member is not limited to a plate shape. For example, the shape of the second member may be a rectangular parallelepiped. Moreover, outer shapes of the first and second members are each not limited to a rectangle. For example, at least one of the outer shape of the first member and the outer shape of the second member may be a circle.

In the first embodiment, an example where, for example, the solution 50 is introduced into the gap 6 through the capillary action has been described, but a pump may be used for introducing, for example, the solution 50 into the gap 6.

In the first embodiment, the second plate-shaped member 3 is fixed to the first plate-shaped member 2 with, for example, the bonding agent at a stage of producing the device 1, but the present invention is not limited thereto. The second plate-shaped member 3 may be fixed to the first plate-shaped member 2 only upon causing the interference fringe 60 to appear and upon delivery of the particulates 51 into the gap 6. In this case, the second plate-shaped member 3 may be fixed by a pressure. For example, a pressure for pushing the second plate-shaped member 3 toward the first plate-shaped member 2 may be given by a driving device such as a piezoelectric element. Moreover, in a case where the second plate-shaped member 3 is fixed by a pressure, the second plate-shaped member 3 and the first plate-shaped member 2 are separated from each other after the delivery of the particulates 51 into the gap 6. At this point, the particulates 51 delivered into the gap 6 adhere to at least one of the first plate-shaped member 2 and the second plate-shaped member 3. Therefore, the particulates 51 can be observed when one or both of the first plate-shaped member 2 and the second plate-shaped member 3 are moved to an observation position of an electronic microscope (for example, a position opposite to the objective lens 106 included in the particle size measurement apparatus 100 described with reference to FIG. 9).

(Second Embodiment)

Hereinafter, the second embodiment will be described, focusing on only a point different from that of the first embodiment. The second embodiment differs from the first embodiment only in that surfaces forming a gap 6 of a device 1 according to the second embodiment are subjected to surface modification.

The surface modification of the surfaces forming the gap 6 permits the surfaces forming the gap 6 to have, for example, an anionic, cationic, hydrophobic (non-polar), or hydrophilic (polar) property. The surface modification is achieved by physically or chemically making a coating substance evenly adhere to the surfaces forming the gap 6. The surface modification can be performed by only making a solution, which contains a substance to adhere to the surfaces forming the gap 6, flow into the gap 6 at a normal temperature. Therefore, the surface modification can simply and quickly be carried out.

For example, in a case where the surfaces forming the gap 6 are hydrophilic, upon injection of particulates 51 each having an ionic surface into the gap 6, the particulates 51 may be absorbed to the surfaces forming the gap 6 before trapped at portions of the gap 6 in accordance with sizes of the particulates 51. Therefore, in the case where the surfaces forming the gap 6 are hydrophilic, the surfaces forming the gap 6 are subjected to surface modification to be hydrophobic. This can reliably trap the particulates 51 at the portions of the gap 6 in accordance with the sizes of the particulates 51 even when the particulates 51 each having an ionic surface are injected into the gap 6.

Through the above, the second embodiment has been described. According to the second embodiment, the surfaces forming the gap 6 can appropriately be subjected to surface modification in accordance with the particulates 51 as a measurement target to provide the gap 6 as a flow channel (a path for a fluid such as a liquid and a gas) suitable for the particulates 51 as the measurement target. Therefore, the particulates 51 can reliably be trapped at the portions of the gap 6 in accordance with the sizes of the particulates 51 without depending on a material of the device 1. Therefore, it is possible to accurately measure the particle sizes of the particulates 51.

For example, it has been known that information transmission between cells or compositions uses vesicles of no greater than one micrometer, and vesicle application in a medication field has been studied. For example, study on use of a vesicle for early cancer detection and study on use of a vesicle for a drug delivery system (DDS) have been in progress. However, since the vesicle is very small, it has been difficult to accurately measure a particle size of the vesicle and measure the number of vesicles. It has also been difficult to sample a vesicle to create a sample of the vesicle.

On the contrary, according to the second embodiment, adjusting charges of the surfaces forming the gap 6 through the surface modification permits trapping of the vesicles at portions of the gap 6 in accordance with sizes of the vesicles. Then particle size distribution of the vesicles in the gap 6 can be measured when a predetermined reaction liquid is injected into the gap 6 where the vesicles are trapped to perform fluorescent staining of the vesicles. In addition, the number of vesicles in the gap 6 can be measured. Further, after the measurement, a formalin solution can be introduced into the gap 6 to preserve the vesicles as samples. As described above, according to the second embodiment, it is possible to count nano-scaled glunular substances specific to cancer. Therefore, the surface modification is useful for inspections for early cancer detection (breast cancer and prostate cancer in particular).

Moreover, according to the second embodiment, through the surface modification of the surfaces forming the gap 6, properties (for example, the surface charges and hydrophilicity) of surfaces of the particulates 51 can be evaluated. Surface charges of standard polystyrene particles were measured as one example. In the evaluation, 500 nm-polystyrene particles and 2 μm-polystyrene particles were used. First to fifth devices 1 were used. The first to fifth devices 1 each include: a first plate-shaped member 2 and a second plate-shaped member 3 formed of glass plates. Surfaces forming gaps 6 of the respective first to fifth devices 1 have mutually different properties.

Figures 14A, 14B, 14C, 14D, 14E:
FIGS. 14A to 14E show photographs in place of drawings illustrating results of evaluating surface charges of standard polystyrene particles by using a device according to a second embodiment of the present invention.

FIG. 14A shows a photographed image of the polystyrene particles in the gap 6 of the first device 1. The first device 1 has the surfaces forming the gap 6 not subjected to surface modification. Therefore, the surfaces forming the gap 6 in the first device 1 are hydrophilic, untreated glass surfaces. As is clear from FIG. 14A, in a case where the surfaces forming the gap 6 are hydrophilic, the 500 nm-polystyrene particles and the 2 μm-polystyrene particles were trapped at portions of the gap 6 in accordance with respective sizes of the two types of polystyrene particles.

FIG. 14B shows a photographed image of the polystyrene particles in the gap 6 of the second device 1. In the second device 1, the surfaces forming the gap 6 were subjected to surface modification by making a solution of sodium lauryl sulfate (a SDS solution) flow into the gap 6 (a flow channel). Therefore, the surfaces forming the gap 6 in the second device 1 are anionic glass surfaces. As is clear from FIG. 14B, in a case where the surfaces forming the gap 6 are anionic, the 500 nm-polystyrene particles and the 2 μm-polystyrene particles were trapped at the portions of the gap 6 in accordance with the respective sizes of the two types of polystyrene particles.

FIG. 14C shows a photographed image of the polystyrene particles in the gap 6 of the third device 1. The third device 1 has the surfaces forming the gap 6 subjected to surface modification by myristyltrimethylammonium as one type of a cationic surfactant. Therefore, the surfaces forming the gap 6 in the third device 1 are cationic glass surfaces. As is clear from FIG. 14C, in a case where the surfaces forming the gap 6 are cationic, the 2 μm-polystyrene particles were absorbed to the surfaces forming the gap 6 before trapped at the portion of the gap 6 in accordance with the size of the 2 μm-polystyrene particles.

FIG. 14D shows a photographed image of the polystyrene particles in the gap 6 of the fourth device 1. The fourth device 1 has the surfaces forming the gap 6 subjected to surface modification by Triton-X as one type of a non-ionic surfactant. Therefore, the surfaces forming the gap 6 in the fourth device 1 are non-ionic glass surfaces. As is clear from FIG. 14D, in a case where the surfaces forming the gap 6 are non-ioninc, the 500 nm-polystyrene particles and the 2 μm-polystyrene particles were trapped at the portions of the gap 6 in accordance with the respective sizes of the two types of polystyrene particles.

FIG. 14E shows a photographed image of the polystyrene particles in the gap 6 of the fifth device 1. The fifth device 1 has the surfaces forming the gap 6 subjected to surface modification by SurfaSil as one type of hydrophobizing agent. Therefore, the surfaces forming the gap 6 in the fifth device 1 are hydrophobic glass surfaces. As is clear from FIG. 14E, in a case where the surfaces forming the gap 6 are hydrophobic, the 500 nm-polystyrene particles and the 2 μm-polystyrene particles were trapped at the portions of the gap 6 in accordance with the respective sizes of the two types of polystyrene particles.

As is clear from FIGS. 14A to 14E, in a case where the surfaces forming the gap 6 are cationic, the polystyrene particles were absorbed to the surfaces forming the gap 6 before trapped at the portions of the gap 6 in accordance with the sizes of the of polystyrene particles. Therefore, it can be understood that surfaces of the polystyrene particles are negatively charged.

As described above, according to the second embodiment, the surface properties of the particulates 51 can be observed based on behavior of the particulates 51 in the flow channels (the gaps 6) having mutually different properties.

(Third Embodiment)

Hereinafter, the third embodiment will be described, focusing on only a point different from that of the first embodiment. The third embodiment differs from the first embodiment only in that a device 1 according to the third embodiment further includes a liquid absorbent substance 8 provided on an outer side of the other end 6*b* of a gap 6.

Figure 15:
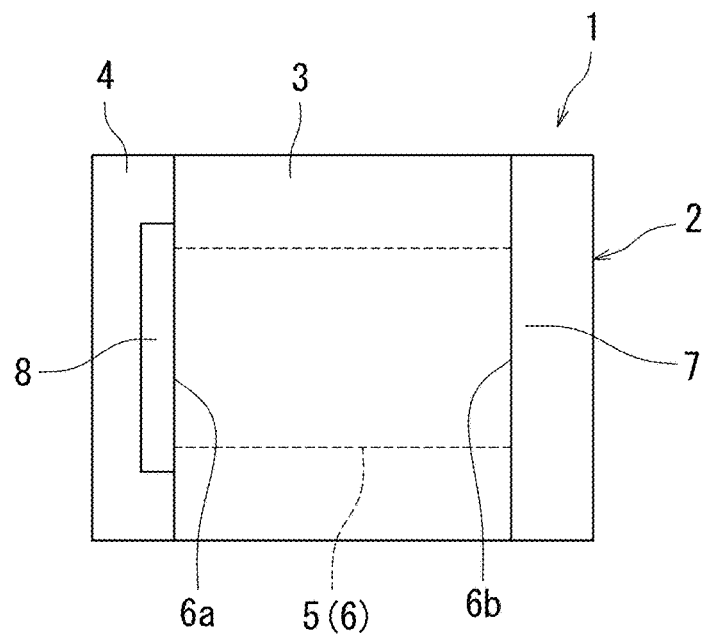
FIG. 15 is a top view schematically illustrating one example of a device according to a third embodiment of the present invention.
Figure 16:
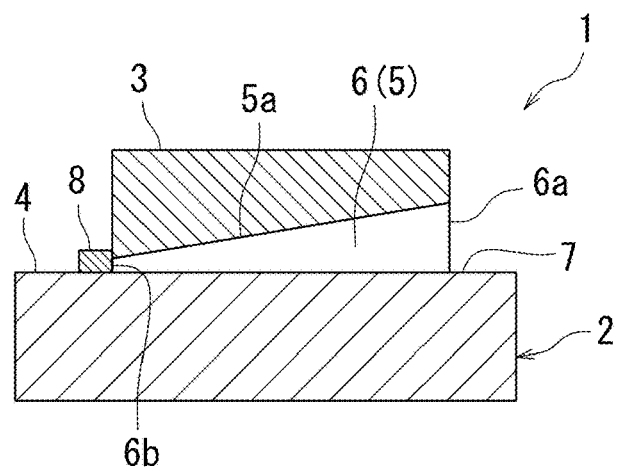
FIG. 16 is a cross-sectional view schematically illustrating one example of the device according to the third embodiment of the present invention.

FIG. 15 is a top view schematically illustrating one example of the device 1 according to the third embodiment of the present invention, and FIG. 16 is a cross-sectional view schematically illustrating the one example of the device 1 according to the third embodiment of the present invention. As illustrated in FIGS. 15 and 16, the liquid absorbent substance 8 is provided on the outer side of the other end 6*b* of the gap 6 in the third embodiment.

The liquid absorbent substance 8 is a substance capable of absorbing liquids. The liquid absorbent substance 8 is provided outside of the gap 6 in a manner such as to be located adjacently to the other end 6*b* of the gap 6. Note that no limitation is placed on the liquid absorbent substance 8 so long as the liquid absorbent substance 8 is capable of absorbing liquids. The liquid absorbent substance 8 may be a substance that includes at least one of, for example, paper, silica gel, and a high molecular polymer.

The liquid absorbent substance 8 can strengthen a driving force for moving particulates 51 toward a narrow side (the other end 6*b*) of the gap 6. Specifically, as described in the first embodiment, upon dripping of a solution 50 including the particulates 51 and a solvent 52 onto a solution introduction part 7 of a first plate-shaped member 2, the device 1 moves the particulates 51 toward the narrow side (the other end 6*b*) of the gap 6 by utilizing, as the driving force, a force based on a capillary action by which the solvent 52 is sucked into the gap 6. According to the third embodiment, the liquid absorbent substance 8 absorbs the solvent 52, which can therefore strengthen the driving force. Therefore, a flow of the solvent 52 becomes faster, permitting shortening of time required for the particulates 51 to be trapped in the gap 6. More specifically, the solvent 52 of the solution 50 dripped onto the solution introduction part 7 is sucked toward the other end 6*b* of the gap 6 through the capillary action of the gap 6. Then the solvent 52 made flow into an opening in the other end 6*b* of the gap 6 is further absorbed by the liquid absorbent substance 8. Therefore, the driving force for moving the particulates 51 toward the other end 6*b* of the gap 6 increases.

There is limitation on an amount of the solvent 52 that can be absorbed by the liquid absorbent substance 8. In a case where an absorbing force of the liquid absorbent substance 8 decreases due to the absorbed solvent 52 not being removed from the liquid absorbent substance 8, the solvent 52 absorbed by the liquid absorbent substance 8 is preferably evaporated. This can maintain the absorbing force of the liquid absorbent substance 8. That is, the evaporation of the solvent 52 absorbed by the liquid absorbent substance 8 permits the liquid absorbent substance 8 to continuously absorb the solvent 52 in the gap 6. A flow rate of the solution 50 is thus maintained. This can shorten the time required for the particulates 51 to be trapped in the gap 6 and also can reliably trap the particulates 51 in the gap 6. For example, heating or wind drying is preferable as means adapted to evaporate the solvent 52. Moreover, in view of promoting the evaporation, a volatile solvent 52 is preferably used.

Through the above, the third embodiment has been described. Note that a recess on which the liquid absorbent substance 8 is provided may be formed on the first plate-shaped member 2. In this case, the liquid absorbent substance 8 may be projected or not projected from the recess. The recess may be formed by, for example, cutting the first plate-shaped member 2. In addition, surfaces forming the gap 6 may be subjected to surface modification in the same manner, as is the case with the second embodiment.

(Fourth Embodiment)

Hereinafter, the fourth embodiment will be described, focusing on only a point different from that of the first embodiment. The fourth embodiment differs from the first embodiment in that a first plate-shaped member 2 according to the fourth embodiment has a groove 10.

Figure 17:
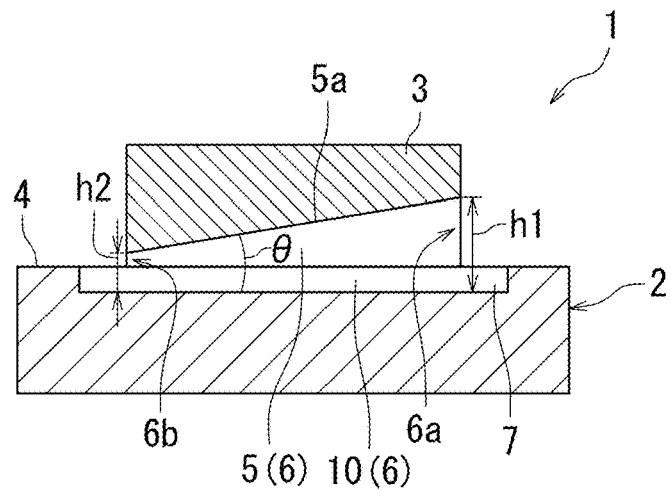
FIG. 17 is a cross-sectional view schematically illustrating one example of a device according to a fourth embodiment of the present invention.

FIG. 17 is a cross-sectional view schematically illustrating one example of a device 1 according to the fourth embodiment of the present invention. As illustrated in FIG. 17, the groove 10 is formed on a main surface 4 of the first plate-shaped member 2 in the fourth embodiment. The groove 10 has a flat bottom surface. The groove 10 can be formed by, for example, cutting a plate-shaped member as a material of the first plate-shaped member 2. Note that the first plate-shaped member 2 may be fabricated by a mold. A portion of an inner surface of the clamped mold corresponding to a surface of the first plate-shaped member 2 on which the groove 10 is formed has a projection corresponding to the groove 10. For example, resin may be filled in the mold to produce the first plate-shaped member 2. The fabrication of the first plate-shaped member 2 with the mold makes it easy to mass-produce the devices 1.

The groove 10 of the first plate-shaped member 2 forms a wedge-shaped gap 6 together with a groove 5 of a second plate-shaped member 3. Openings on one end 6a and another end 6b of the gap 6 are formed by the groove 10 and openings at both ends of the groove 5. The groove 10 extends further to an outer side of each of the one end 6a and the other end 6b of the gap 6. Of the groove 10, a portion on the outer side of the one end 6a of the gap 6 is used as a solution introduction part 7.

Figure 18:
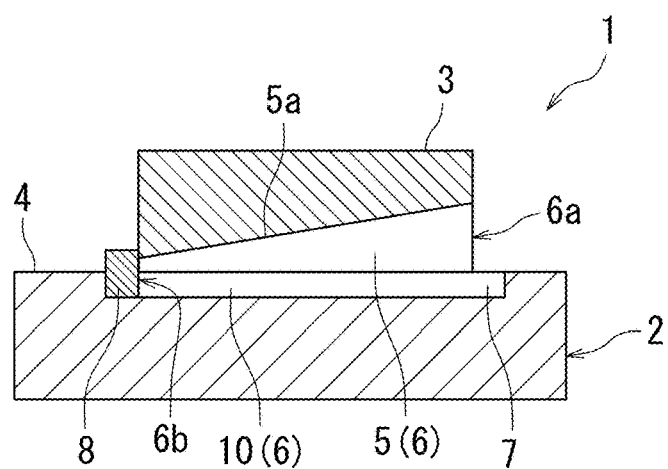
FIG. 18 is a cross-sectional view schematically illustrating another Example 1 of the device according to the fourth embodiment of the present invention.

As is the case with the third embodiment, a liquid absorbent substance 8 may be provided outside of the gap 6 adjacently to the other end 6b of the gap 6. FIG. 18 is a cross-sectional view schematically illustrating another Example 1 of the device 1 according to the fourth embodiment of the present invention. A liquid absorbent substance 8 is provided in the groove 10 of the first plate-shaped member 2 in the fourth embodiment. More specifically, the liquid absorbent substance 8 is provided at a portion of the groove 10 on the outer side of the other end 6b of the gap 6.

Figure 19:
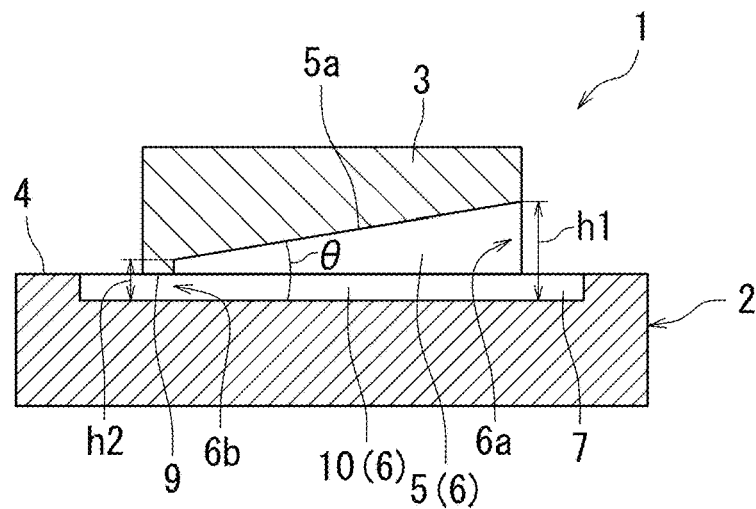
FIG. 19 is a cross-sectional view schematically illustrating another Example 2 of the device according to the fourth embodiment of the present invention.

One end of the groove 5 of the second plate-shaped member 3 may not be open. FIG. 19 is a cross-sectional view schematically illustrating another Example 2 of the device 1 according to the fourth embodiment of the present invention. As illustrated in FIG. 19, the groove 5 is not open to a side surface of the second plate-shaped member 3 on a narrow side (the other end 6b) of the wedge-shaped gap 6. Even with such configuration, the wedge-shaped gap 6 can be formed by the groove 10 of the first plate-shaped member 2 and the groove 5 of the second plate-shaped member 3. Note that one end of an inclined surface 5a of the second plate-shaped member 3 may be connected to a main surface 9 of the second plate-shaped member 3. The main surface 9 of the second plate-shaped member 3 is a surface opposite to the first plate-shaped member 2.

Figure 20:
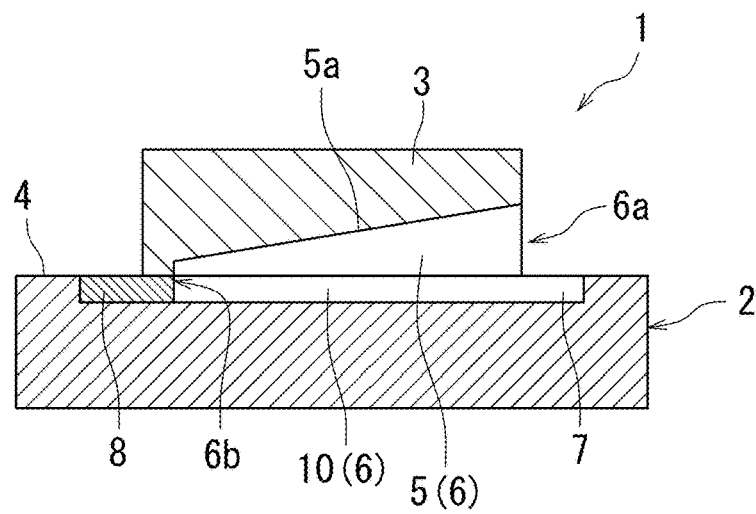
FIG. 20 is a cross-sectional view schematically illustrating the other Example 3 of the device according to the fourth embodiment of the present invention.

Also in a case where one end of the groove 5 of the second plate-shaped member 3 is not open, as is the case with the third embodiment, the liquid absorbent substance 8 can be provided outside of the gap 6 adjacently to the other end 6b of the gap 6. FIG. 20 is a cross-sectional view schematically illustrating another Example 3 of the device 1 according to the fourth embodiment of the present invention. As is the case with the device 1 described with reference to FIG. 18, the liquid absorbent substance 8 is provided in the groove 10 of the first plate-shaped member 2. More specifically, the liquid absorbent substance 8 is provided from a position adjacent to the other end 6b of the gap 6 to an outside of the second plate-shaped member 3.

Through the above, the fourth embodiment has been described. According to the fourth embodiment, it is possible to set an angle θ of the wedge-shaped gap 6, which hardly results in variation in the height h of the gap 6 between a plurality of devices 1. Therefore, variation in the devices 1 between different product lots can be suppressed.

Note that the groove 10 may extend from one end to another end of the first plate-shaped member 2 in a direction in which the inclined surface 5a of the second plate-shaped member 3 is inclined. In addition, as is the case with the second embodiment, surfaces forming the gap 6 may be subjected to surface modification. In this case, an inner surface of the groove 5 of the second plate-shaped member 3 and an inner surface of the groove 10 of the first plate-shaped member 2 are subjected to the surface modification.

(Fifth Embodiment)

Hereinafter, the fifth embodiment will be described, focusing on only a point different from that of the first embodiment. The fifth embodiment differs from the first embodiment in that a first plate-shaped member 2 according to the fifth embodiment has a recess 11.

Figure 21:
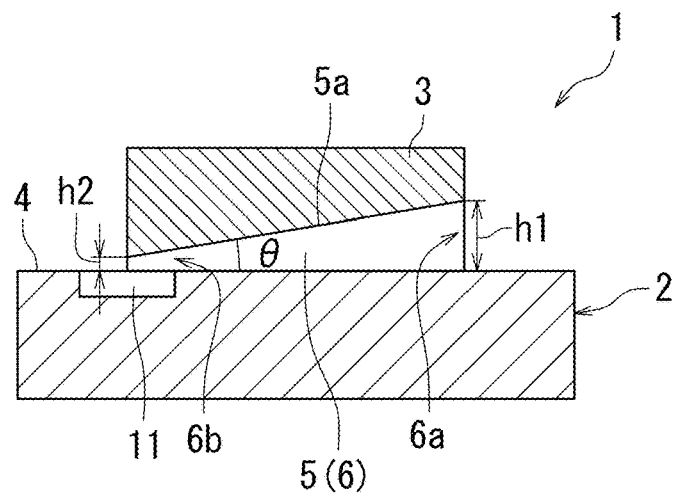
FIG. 21 is a cross-sectional view schematically illustrating one example of a device according to a fifth embodiment of the present invention.

FIG. 21 is a cross-sectional view schematically illustrating one example of a device 1 according to the fifth embodiment of the present invention. As illustrated in FIG. 21, the recess 11 is formed on a main surface 4 of the first plate-shaped member 2 in the fifth embodiment. The recess 11 is connected to a groove 5 on a narrowest side (the other end 6b) of a gap 6 and communicates with the air outside of a second plate-shaped member 3. The recess 11 can be formed by, for example, cutting a plate-shaped member as a material of the first plate-shaped member 2. Note that the first plate-shaped member 2 may be fabricated by a mold. A portion of an inner surface of the clamped mold corresponding to a surface of the first plate-shaped member 2 on which the recess 11 is formed has a projection corresponding to the recess 11. For example, resin may be filled in the mold to produce the first plate-shaped member 2. The fabrication of the first plate-shaped member 2 with the mold makes it easy to mass-produce the devices 1.

An opening in the other end 6b of the gap 6 is formed in the middle of the groove 5 of the second plate-shaped member 3 in the fifth embodiment. That is, the opening in the other end 6b of the gap 6 is formed inside of the device 1.

Figure 22:
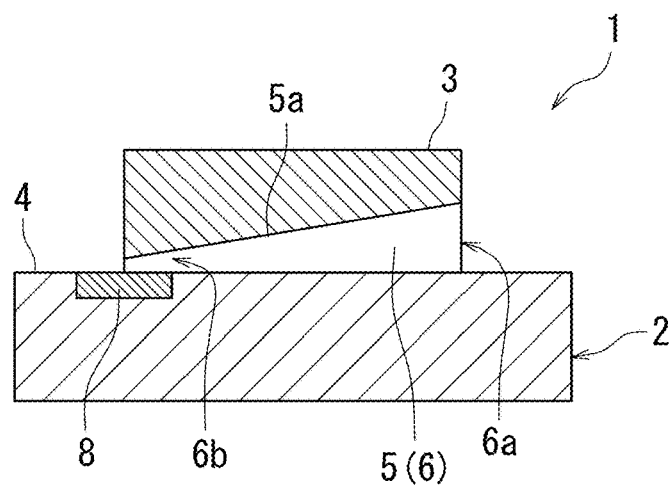
FIG. 22 is a cross-sectional view schematically illustrating another Example 1 of the device according to the fifth embodiment of the present invention.

As is the case with the third embodiment, a liquid absorbent substance 8 may be provided outside of the gap 6 adjacently to the other end 6b of the gap 6. FIG. 22 is a cross-sectional view schematically illustrating another Example 1 of the device 1 according to the fifth embodiment of the present invention. A liquid absorbent substance 8 is provided in the recess 11 of the first plate-shaped member 2 in the fifth embodiment. More specifically, the liquid absorbent substance 8 is provided from a position adjacent to the other end 6b of the gap 6 to an outside of the second plate-shaped member 3.

Figure 23:
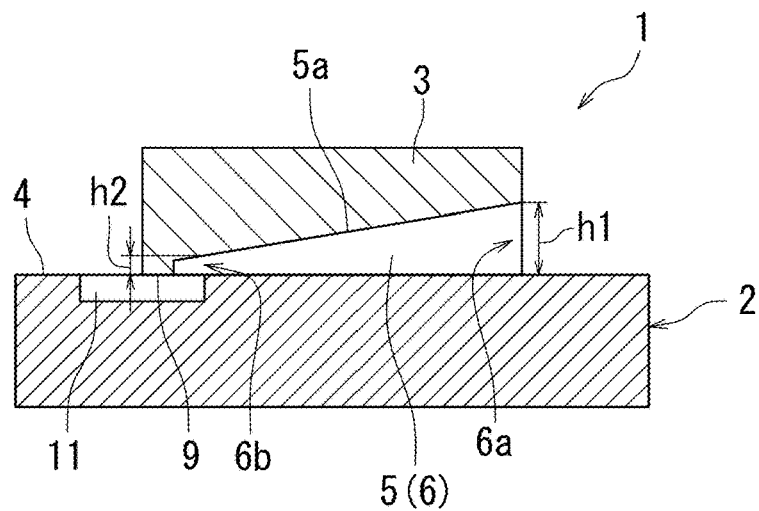
FIG. 23 is a cross-sectional view schematically illustrating another Example 2 of the device according to the fifth embodiment of the present invention.

Note that one end of the groove 5 of the second plate-shaped member 3 may not be open. FIG. 23 is a cross-sectional view schematically illustrating another Example 2 of the device 1 according to the fifth embodiment of the present invention. As illustrated in FIG. 23, the groove 5 is not open to a side surface of the second plate-shaped member 3 on the narrow side (the other end 6b) of the wedge-shaped gap 6. Even with such configuration, the recess 11 communicates with the air outside of the second plate-shaped member 3 while connected to the groove 5 on the narrowest side (the other end 6b) of the gap 6, thus making it possible to move particulates 51 included in a solution 50 toward the other end 6b of the gap 6 and trap the particulates 51 at portions of the gap 6 in accordance with sizes of the particulates 51. Note that one end of an inclined surface 5a of the second plate-shaped member 3 may be connected to a main surface 9 of the second plate-shaped member 3. The main surface 9 of the second plate-shaped member 3 is a surface opposite to the first plate-shaped member 2.

Figure 24:
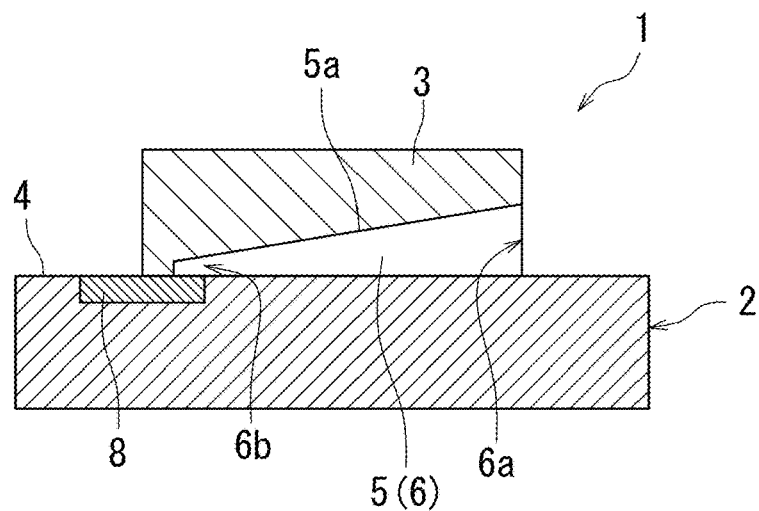
FIG. 24 is a cross-sectional view schematically illustrating the other Example 3 of the device according to the fifth embodiment of the present invention.

Also in a case where one end of the groove 5 of the second plate-shaped member 3 is not open, as is the case with the third embodiment, the liquid absorbent substance 8 can be provided outside of the gap 6 adjacently to the other end 6b of the gap 6. FIG. 24 is a cross-sectional view schematically illustrating another Example 3 of the device 1 according to the fifth embodiment of the present invention. As is the case with the device 1 described with reference to FIG. 22, the liquid absorbent substance 8 is provided in the recess 11 of the first plate-shaped member 2. More specifically, the liquid absorbent substance 8 is provided from a position adjacent to the other end 6b of the gap 6 to an outside of the second plate-shaped member 3.

Through the above, the fifth embodiment has been described. With the fifth embodiment, it is possible to set an angle θ of the wedge-shaped gap 6, which hardly results in variation in the height h of the gap 6 between a plurality of devices 1. Therefore, variation in the devices 1 between different product lots can be suppressed.

In addition, as is the case with the second embodiment, surfaces forming the gap 6 may be subjected to surface modification.

(Sixth Embodiment)

Hereinafter, the sixth embodiment will be described, focusing on only a point different from that of the first embodiment. The sixth embodiment differs from the first embodiment in that a plurality of grooves 5 are formed on a second plate-shaped member 3 according to the sixth embodiment.

Figure 25:
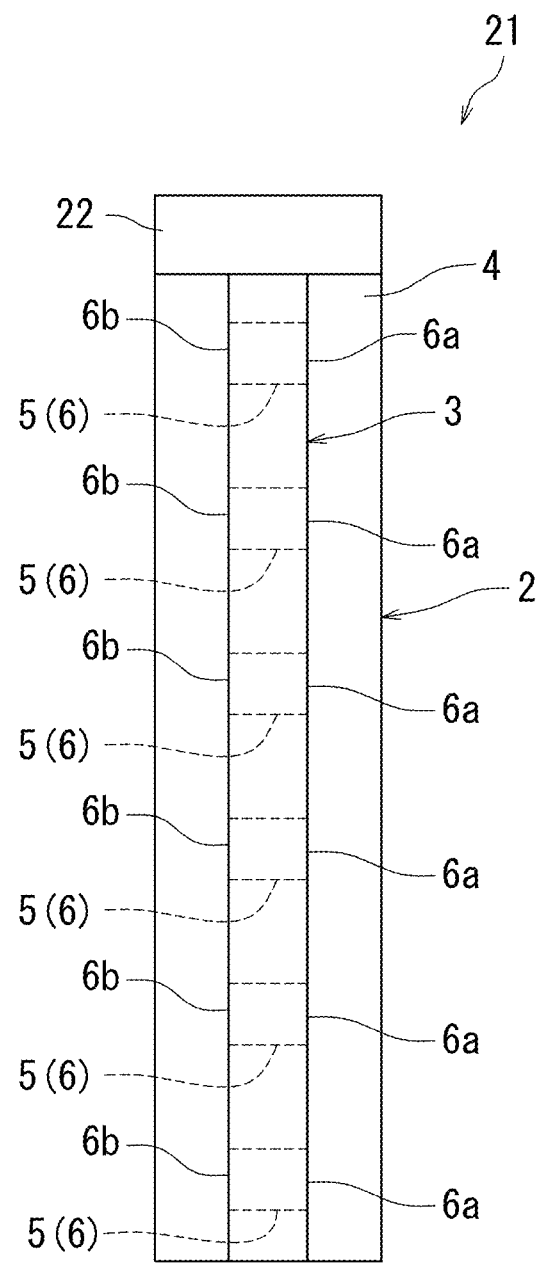
FIG. 25 is a top view schematically illustrating one example of a device according to a sixth embodiment of the present invention.

FIG. 25 is a top view schematically illustrating one example of a device 21 according to the sixth embodiment of the present invention. As illustrated in FIG. 25, the plurality of grooves 5 are formed on the second plate-shaped member 3 in the sixth embodiment. The plurality of grooves 5 are arranged along the direction orthogonal to a direction in which inclined surfaces 5a are inclined. Therefore, the device 21 has a plurality of gaps 6 provided along the direction orthogonal to the direction in which the inclined surfaces 5a are inclined. That is, the device 21 has the same configuration as configuration such that a plurality of devices 1 are connected together in the direction orthogonal to the direction in which the inclined surfaces 5a are inclined.

The device 21 also has a handle part 22 at one end thereof in a direction in which the plurality of gaps 6 are arrayed. Providing the device 21 with the handle part 22 makes it easy for an operator to perform an operation of conveying the device 21, an operation of positioning the device 21, etc. Note that, however, the handle part 22 may be omitted.

The second plate-shaped member 3 of the device 21 can be fabricated by executing, a plurality of times, the process of cutting the plate-shaped member 3a described with reference to FIG. 4B. Specifically, the plate-shaped member 3a (one example of the to-be-processed member) as a material of the second plate-shaped member 3 is placed still while angled at a fixed inclination angle θ, and a tool 43 is moved horizontally to the inclined plate-shaped member 3a to cut the plate-shaped member 3a. As a result, one groove 5 having an inclined surface 5a angled at the fixed inclination angle θ is formed. The cutting process is carried out a plurality of times to form the plurality of grooves 5 at the plate-shaped member 3a along the direction orthogonal to a direction in which inclined surfaces 5a are inclined. As a result, the second plate-shaped member 3 of the device 21 is fabricated.

Note that the second plate-shaped member 3 may be fabricated by a mold. A portion of an inner surface of the clamped mold corresponding to a surface of the second plate-shaped member 3 on which the plurality of grooves 5 are formed has projections respectively corresponding to the grooves 5. For example, resin may be filled in the mold to produce the second plate-shaped member 3. The fabrication of the second plate-shaped member 3 with the mold makes it easy to mass-produce the devices 21.

Through the above, the sixth embodiment has been described. According to the sixth embodiment, it is possible to set an angle θ of the wedge-shaped gaps 6, which hardly results in variation in the height h of the gaps 6 between the plurality of devices 21. Therefore, variation in the devices 21 between different product lots can be suppressed. Further, variation in the height h of the gap 6 also hardly occurs between the plurality of gaps 6 formed in one device 21.

Note that the device 21 having the same configuration as the configuration such that the plurality of devices 1 according to the first embodiment are connected together has been described in the sixth embodiment, but the device 21 may have the same configuration as configuration such that a plurality of devices 1 according to the fourth embodiment or a plurality of devices 1 according to the fifth embodiment are connected together. Alternatively, the device 21 may have configuration that combines two or more of the device 1 according to the first embodiment, the device 1 according to the fourth embodiment, and the device 1 according to the fifth embodiment.

The plurality of wedge-shaped gaps 6 formed in the single device 21 may not be identical to each other. For example, the plurality of wedge-shaped gaps 6 may have mutually different angles θ, lengths L1, or widths W. Similarly, opening heights h1 of one ends 6a of the plurality of wedge-shaped gaps 6 may be mutually different from each other, and opening heights h2 of another ends 6b of the plurality of wedge-shaped gaps 6 may be mutually different from each other.

In addition, as is the case with the second embodiment, surfaces respectively forming the plurality of gaps 6 may be subjected to surface modification. In this case, the surfaces respectively forming the plurality of gaps 6 may be subjected to mutually different types of surface modification.

Figure 26:
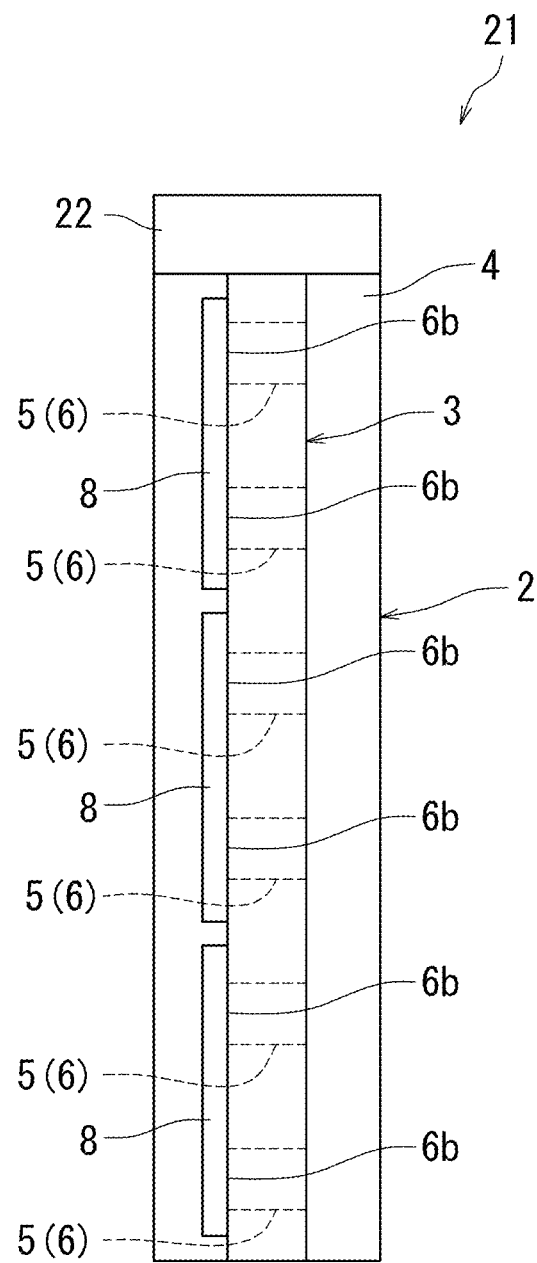
FIG. 26 is a top view schematically illustrating another Example 1 of the device according to the sixth embodiment of the present invention.
Figure 27:
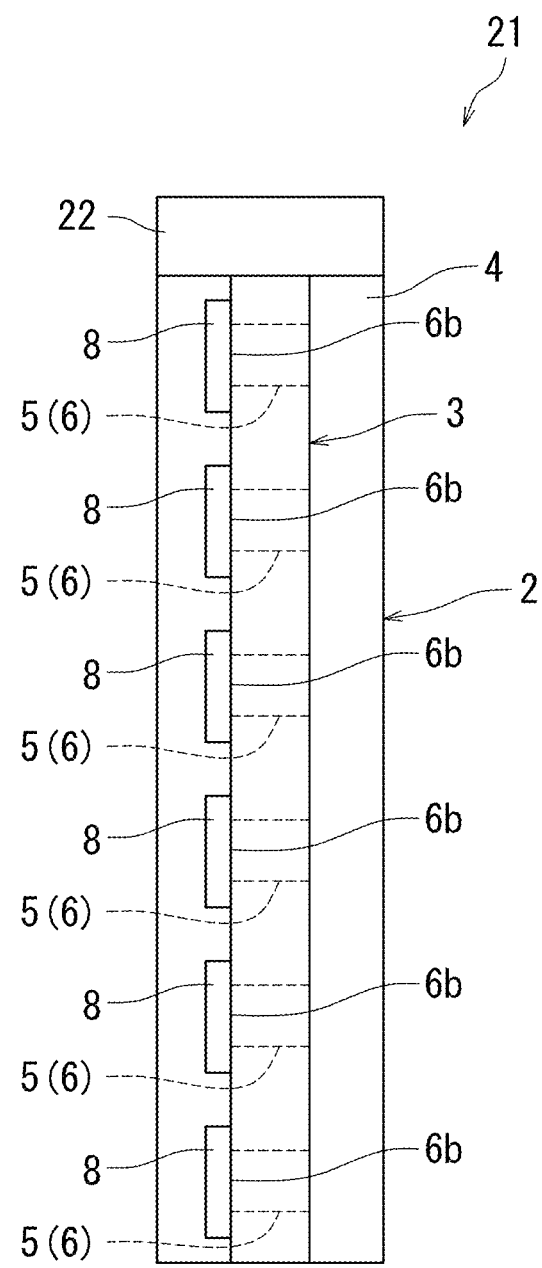
FIG. 27 is a top view schematically illustrating another Example 2 of the device according to the sixth embodiment of the present invention.
Figure 28:
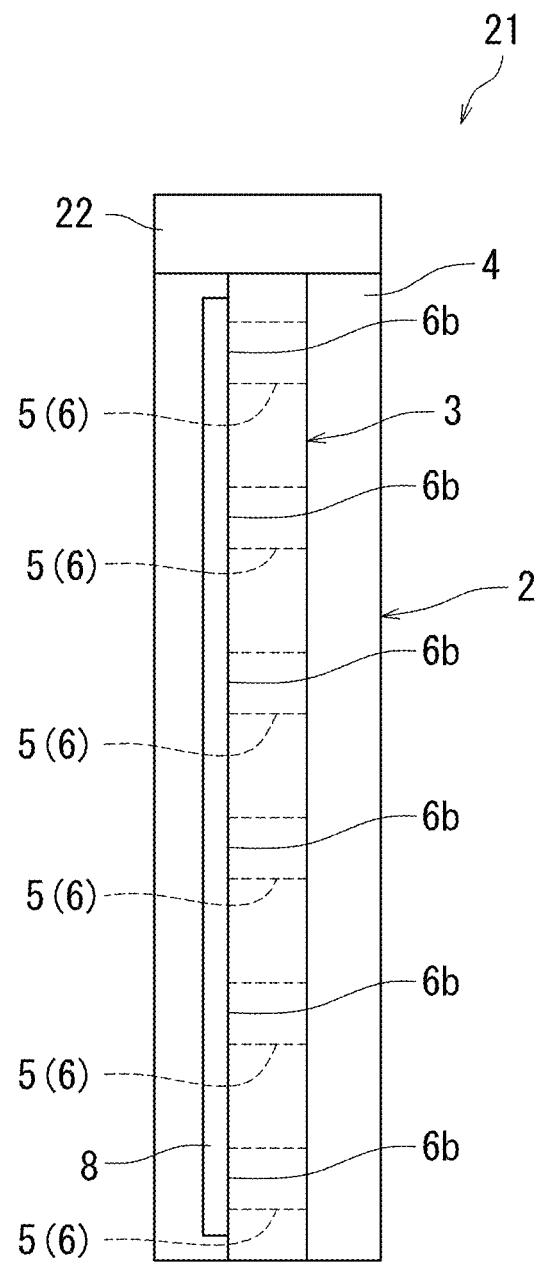
FIG. 28 is a top view schematically illustrating the other Example 3 of the device according to the sixth embodiment of the present invention.

As is the case with the third embodiment, a liquid absorbent substance 8 may be provided outside of each gap 6 adjacently to the other end 6b of each gap 6. FIG. 26 is a top view schematically illustrating another Example 1 of the device 21 according to the sixth embodiment of the present invention, FIG. 27 is a top view schematically illustrating another Example 2 of the device 21 according to the sixth embodiment of the present invention, and FIG. 28 is a top view schematically illustrating another Example 3 of the device 21 according to the sixth embodiment of the present invention. As illustrated in FIG. 26, a plurality of liquid absorbent substances 8 that are long in the direction in which the plurality of gaps 6 are arrayed may be provided on a main surface 4 of a first plate-shaped member 2, or as illustrated in FIG. 27, a liquid absorbent substance 8 may be provided for each gap 6. Alternatively, as illustrated in FIG. 28, one liquid absorbent substance 8 may be provided which is opposite to openings in the other ends 6b of all the gaps 6.

(Seventh Embodiment)

Figure 29:
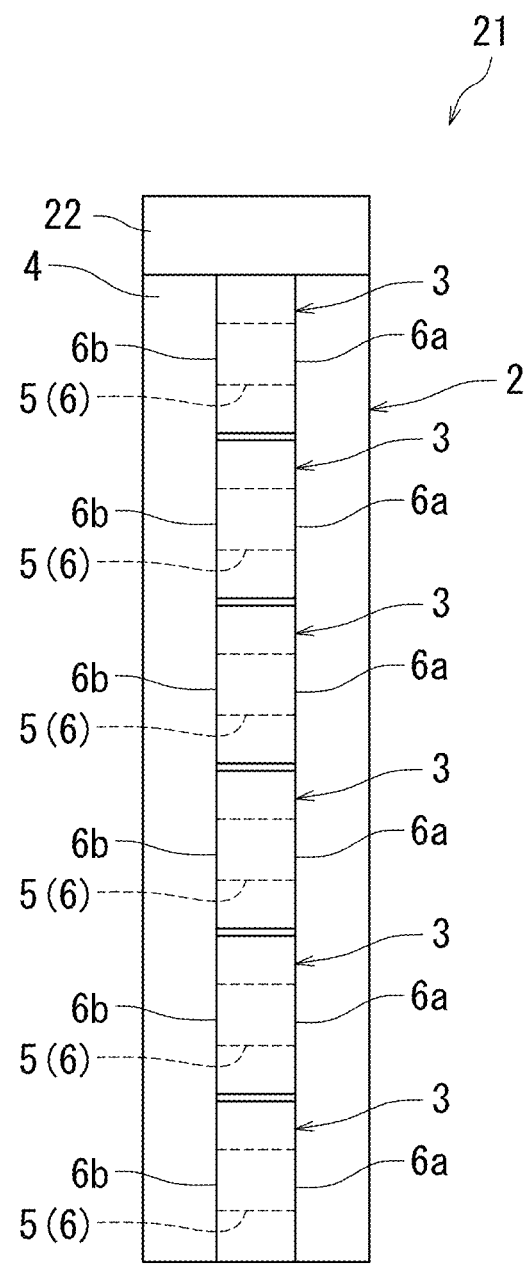
FIG. 29 is a top view schematically illustrating one example of a device according to a seventh embodiment of the present invention.

In the sixth embodiment, the single second plate-shaped member 3 on which the plurality of grooves 5 are formed is used, but the present invention is not limited thereto. FIG. 29 is a top view schematically illustrating one example of a device 21 according to the seventh embodiment of the present invention. The seventh embodiment differs from the sixth embodiment only in that each second plate-shaped member 3 on which one groove 5 is formed is fixed to one first plate-shaped member 2.

With such configuration, it is possible to set an angle θ of wedge-shaped gaps 6, which hardly results in variation in the height h of the gaps 6 between the plurality of devices 21. Therefore, variation in the devices 21 between different product lots can be suppressed. Further, variation in the height h of the gap 6 also hardly occurs between the plurality of gaps 6 formed in the single device 21.

Although not illustrated, each second plate-shaped member 3 on which a plurality of grooves 5 are formed may be fixed to the single first plate-shaped member 2.

(Eighth Embodiment)

As described in the first embodiment, upon entrance of a light beam of a single wavelength to the device 1, the interference fringe 60 repeatedly having a bright line and a dark line is formed (see FIG. 7). The relationship between the bright lines and the dark lines of the interference fringe 60 is expressed by the formulae (1) and (2) as described in the first embodiment. According to the formula (2), a position where the first bright line appears is located at a position where m is 0 (that is, $h=\lambda/4n$). Only the dark lines are observed before the height h of the gap 6 reaches a height that satisfies the aforementioned condition, and thus a beginning portion of the interference fringe 60 turns black as illustrated in a region a of FIG. 7, which may result in difficulties in observing the first dark line. In this case, it is not known how many dark lines there are before the observed dark line, resulting in failure to obtain the height h of the gap 6 according to the formula (1). Therefore, it is required to obtain the accurate number of dark lines. Hereinafter, a particle size measurement method under condition that it is difficult to observe the first dark line will be described.

In a case where it is difficult to observe the first dark line, a plurality of light beams having mutually different wavelengths are irradiated to the device 1 to cause a plurality of interference fringes 60 to appear. Each dark line of the plurality of interference fringes 60 appears for each half wavelength of the corresponding wavelength. Therefore, the respective dark lines of the plurality of interference fringes 60 overlap at a position corresponding to a common multiple of the respective half-wavelengths of the mutually different wavelengths. Therefore, positions where the respective first dark lines of the plurality of interference fringes 60 appear can be determined based on the position where the respective dark lines of the plurality of interference fringes 60 overlap. Therefore, use of one of the plurality of light beams for the particle size measurement makes it possible to accurately measure a particle size.

For example, in a case where two interference fringes 60 are caused to appear by using two monochromatic light beams having mutually different wavelengths, dark lines of the two interference fringes 60 first overlap at a position corresponding to a minimum common multiple of respective half-wavelengths of the two wavelengths. Therefore, positions where the first dark lines of the two interference fringes 60 appear can be determined based on the minimum common multiple of the respective half-wavelengths of the two wavelengths. Therefore, even in a case where it is difficult to observe the first dark line, it is possible to accurately determine how many dark lines there are before the observed dark line. Thus, even in a case where variation in the devices 1 between different product lots is occurring, it is possible to accurately measure a particle size.

Figure 30A:
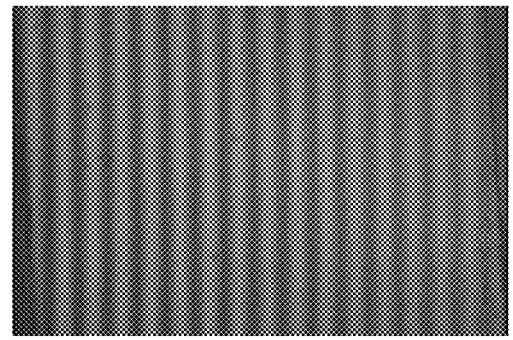
FIGS. 30A to 30C show photographs in place of drawings illustrating two types of interference fringes according to an eighth embodiment of the present invention.
Figure 30B:
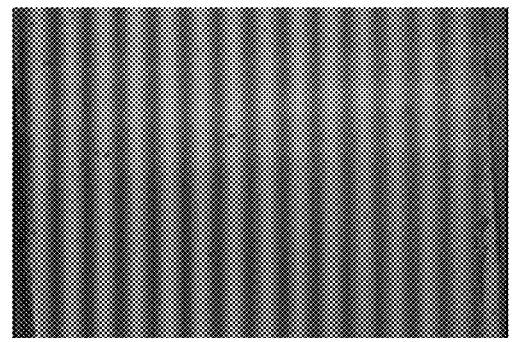
Figure 30C:
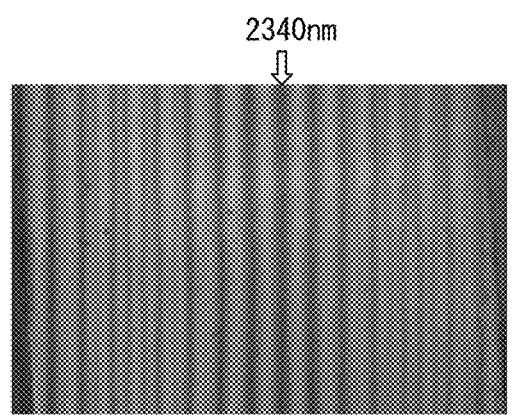

As one example, two interference fringes 60 were caused to appear by using a monochromatic light beam of 520 nm in wavelength and a monochromatic light beam of 585 nm in wavelength. FIGS. 30A to 30C show photographed images. FIG. 30A shows the interference fringe caused to appear as a result of irradiating the device 1 with the monochromatic light beam of 520 nm in wavelength. Hereinafter, the interference fringe caused to appear as a result of irradiating the device 1 with the monochromatic light beam of 520 nm in wavelength may be described as the first interference fringe. When the monochromatic light beam of 520 nm in wavelength is irradiated, an interval between dark lines of the interference fringe (the first interference fringe) is 260 nm. FIG. 30B shows the interference fringe caused to appear as a result of irradiating the device 1 with the monochromatic light beam of 585 nm in wavelength. Hereinafter, the interference fringe caused to appear as a result of irradiating the monochromatic light beam of 585 nm in wavelength may be described as the second interference fringe. When the monochromatic light beam of 585 nm in wavelength is irradiated, an interval between dark lines of the interference fringe (the second interference fringe) is 292.5 nm. FIG. 30C shows the two interference fringes (the first interference fringe and the second interference fringe) caused to appear as a result of simultaneously irradiating the device 1 with the monochromatic light beam of 520 nm in wavelength and the monochromatic light beam of 585 nm in wavelength. A minimum common multiple of respective half-wavelengths of the two wavelengths 520 nm and 585 nm is 2340 nm. Therefore, by dividing 2340 nm by 260 nm, it is possible to find how many dark lines of the first interference fringe there are before the dark line of the first interference fringe overlapping the dark line of the second interference fringe. Similarly, by dividing 2340 nm by 292.5 nm, it is possible to find how many dark lines of the second interference fringe there are before the dark line of the second interference fringe overlapping the dark line of the first interference fringe. Therefore, the positions where the respective first dark lines of the first interference fringe and the second interference fringe appear can be determined based on the minimum common multiple 2340 nm of the respective half-wavelengths of the two wavelengths 520 nm and 585 nm.

Figure 31:
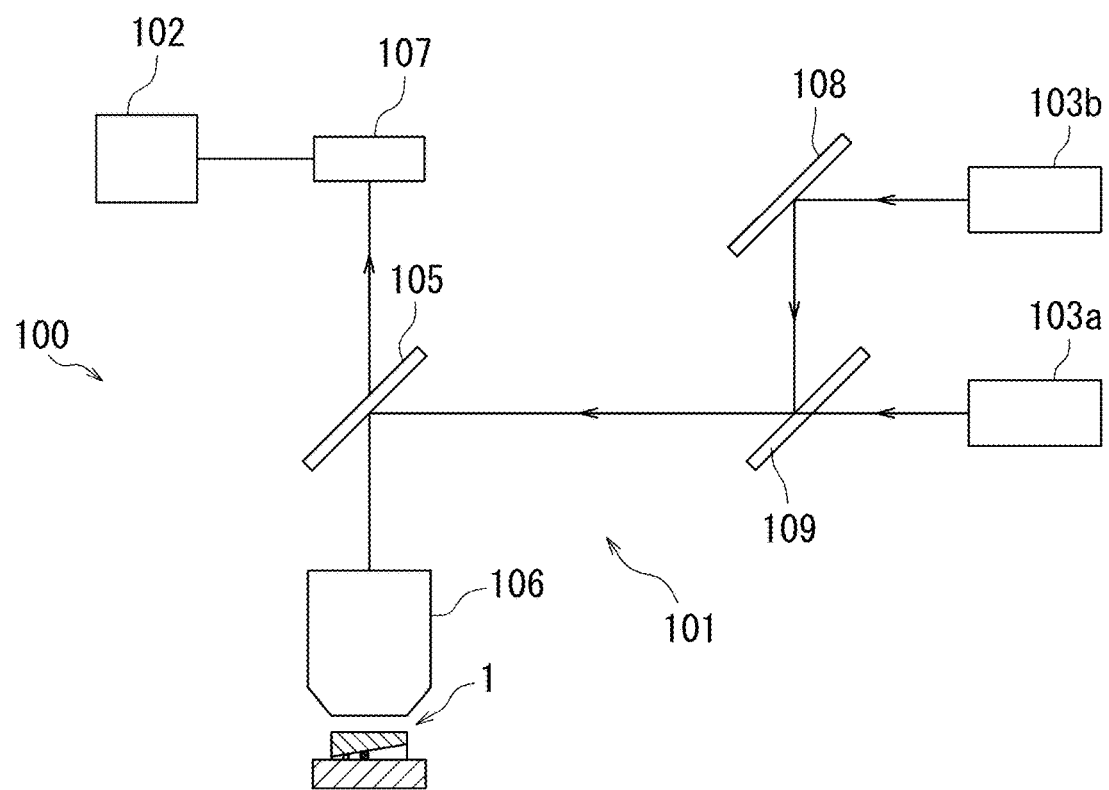
FIG. 31 is a schematic view illustrating one example of configuration of a particle size measurement apparatus according to the eighth embodiment of the present invention.

FIG. 31 is a schematic view illustrating one example of configuration of a particle size measurement apparatus 100 (one example of an observation apparatus) according to the eighth embodiment of the present invention. As illustrated in FIG. 31, an observing optical system 101 includes: two light sources 103a and 103b, a mirror 108, and a mirror 109 in the particle size measurement apparatus 100 according to the eighth embodiment. The two light sources 103a and 103b generate light beams having mutually different single wavelengths. The mirror 108 reflects the light beam, which has been generated from the light source 103b, toward the mirror 109. The mirror 109 transmits the light beam generated from the light source 103a and reflects the light beam generated from the light source 103b.

The particle size measurement apparatus 100 according to the eighth embodiment can simultaneously irradiate the device 1 with the two light beams having the mutually different wavelengths to cause two interference fringes 60 to appear. The camera 107 can photograph the two interference fringes 60.

Note that an analysis section 102 in the particle size measurement apparatus 100 according to the eighth embodiment may have a function of detecting, based on the image, at least one position where respective dark lines of the plurality of interference fringes 60 overlap to determine positions where respective first dark lines of the interference fringes 60 appear.

A filter that permits transmission of a light beam of a predetermined wavelength may be set in a light path of a light beam generated from the light source 103a to the mirror 109. In this case, the light source 103a may not generate a light beam of a single wavelength. Similarly, a filter that permits transmission of a light beam of a predetermined wavelength may be set in a light path of a light beam generated from the light source 3b to the mirror 109. In this case, the light source 103b may not generate a light beam of a single wavelength. Alternatively, one light source that generates a light beam having a broadband wavelength and two filters that permits transmission of light beams of mutually different wavelengths may be used. In this case, a mirror that divides a light path of a light beam generated from the light source into two and a mirror that links together the divided light paths are set, and a filter is set on each light path obtained from the division. This makes it possible to simultaneously irradiate the device 1 with two light beams of mutually different wavelengths.

The eighth embodiment has been described, referring to the example of the device 1 according to the first embodiment, but it is also possible in the devices 1 and 21 according to the second to seventh embodiments to accurately determine how many dark lines there are before the observed dark line.

Figure 32:
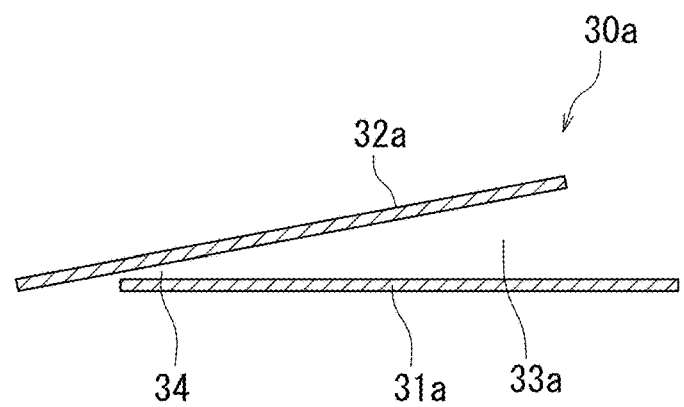
FIG. 32 is a conceptual diagram of another device according to the eighth embodiment of the present invention.

The points described in the eighth embodiment are also applicable to any device other than the devices 1 and 21 according to the first to seventh embodiments. For example, the points described in the eighth embodiment are applicable to a device 30a as illustrated in FIG. 32. FIG. 32 is a conceptual diagram in a cross-sectional view of the other device 30a according to the eighth embodiment of the present invention. The device 30a includes: a first flat plate 31a as one example of the first member; and a second flat plate 32a as one example of the second member. The second flat plate 32a is obliquely superposed on the first flat plate 31a, with a gap 33a formed between the first flat plate 31a and the second flat plate 32a in a manner such as to become continuously narrower. An opening part 34 is formed at a narrowest part of the gap 33a. Upon irradiation of the device 30a with a predetermined light beam, an interference fringe is caused to appear by the gap 33a. A material capable of causing an interference fringe in this manner is selected as a material of the first flat plate 31a and the second flat plate 32a. For example, a glass plate or a plastic plate can be used as a material of the first flat plate 31a and the second flat plate 32a. As is the case with in the devices 1 and 21 according to the first to seventh embodiments, it is also possible in such a device 30a to accurately determine how many dark lines there are before an observed dark line.

Figure 33:
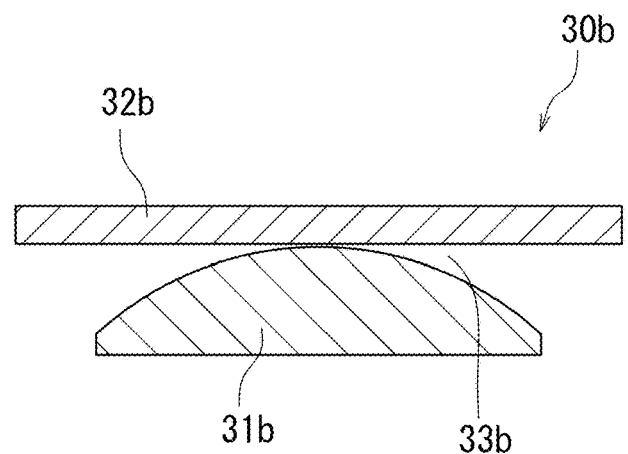
FIG. 33 is a conceptual diagram of still another device according to the eighth embodiment of the present invention.

The points described in the eighth embodiment are also applicable to, for example, a device 30b as illustrated in FIG. 33. FIG. 33 is a conceptual diagram in a cross-sectional view of the other device 30b according to the eighth embodiment of the present invention. The device 30b includes: a lens 31b as one example of the first member; and a flat plate 32b as one example of the second member. A gap 33b that becomes continuously narrower is formed between the lens 31b and the flat plate 32b. Upon irradiation of the device 30b with a predetermined light beam, an interference fringe is caused to appear by the gap 33b. A material capable of causing such an interference fringe to appear is selected as a material of the flat plate 32b. For example, a glass plate or a plastic plate can be used as a material of the flat plate 32b. As is the case with the devices 1 and 21 according to the first to seventh embodiments, it is also possible in such a device 30b to accurately determine how many dark lines there are before an observed dark.

Figure 34:
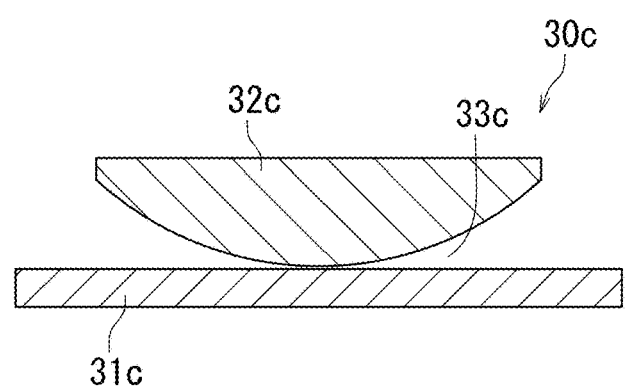
FIG. 34 is a conceptual diagram of still another device according to the eighth embodiment of the present invention.

The points described in the eighth embodiment are also applicable to, for example, a device 30c as illustrated in FIG. 34. FIG. 34 is a conceptual diagram in a cross-sectional view of the other device 30c according to the eighth embodiment of the present invention. The device 30c includes: a flat plate 31c as one example of the first member; and a lens 32c as one example of the second member. A gap 33c that becomes continuously narrower is formed between the flat plate 31c and the lens 32c. Upon irradiation of the device 30c with a predetermined light beam, an interference fringe is caused to appear by the gap 33c. A material capable of causing such an interference fringe to appear is selected as a material of the flat plate 31c. For example, a glass plate or a plastic plate can be used as a material of the flat plate 31c. As is the case with the devices 1 and 21 according to the first to seventh embodiments, it is also possible in such a device 30c to accurately determine how many dark lines there are before an observed dark line.

The points described in the eighth embodiment are also applicable to various fields in which an interference fringe is utilized. For example, application of the points described in the eighth embodiment to a technology of irradiating a light beam to an eyeball and measuring a thickness of a surface film of the eyeball makes it possible to accurately determine how many dark lines there are before an observed dark line in an interference fringe caused to appear on the eyeball.

Through the above, the eighth embodiment has been described. The points described in the eighth embodiment refer to a method that is widely applicable to any target in which an interference fringe appears, and the method includes the following processes. Specifically, the method includes a process of irradiating a plurality of light beams of mutually different wavelengths to a target and causing a plurality of interference fringes to appear on the target by the respective light beams. The method also includes a process of detecting a position where respective dark lines of the plurality of interference fringes overlap. The method also includes a process of determining, based on the detected position where the detected dark lines overlap and based on a common multiple of half-wavelengths of the respective wavelengths, positions where respective first dark lines of the plurality of interference fringes appear.

(Ninth Embodiment)

Figure 35:
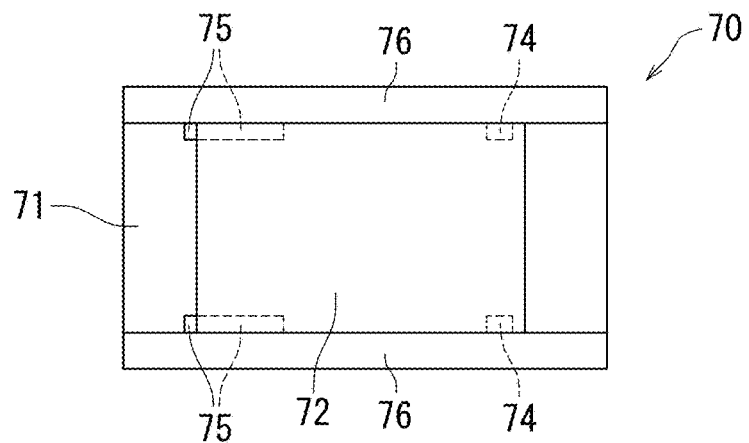
FIG. 35 is a top view schematically illustrating one example of a device according to a ninth embodiment of the present invention.
Figure 36:
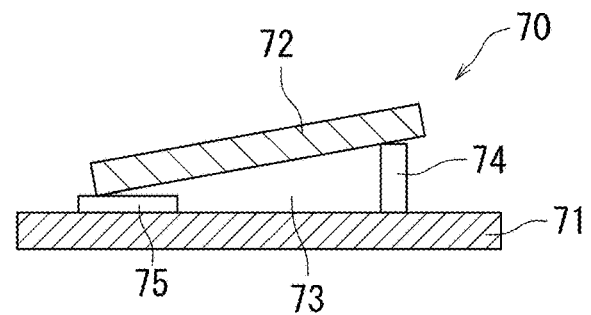
FIG. 36 is a cross-sectional view schematically illustrating one example of the device according to the ninth embodiment of the present invention.
Figure 37:
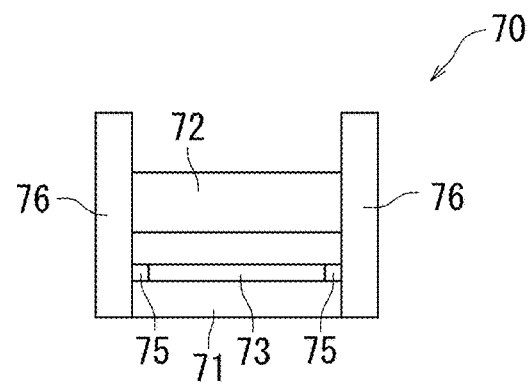
FIG. 37 is a rear view schematically illustrating one example of the device according to the ninth embodiment of the present invention.

Hereinafter, another embodiment of a device according to the present invention will be described with reference to FIGS. 35 to 38. FIG. 35 is a top view schematically illustrating one example of a device 70 according to the ninth embodiment of the present invention, and FIG. 36 is a cross-sectional view schematically illustrating one example of the device 70 according to the ninth embodiment of the present invention. Note that side plates 76 are omitted in FIG. 36 for easier understanding. FIG. 37 is a rear view schematically illustrating one example of the device 70 according to the ninth embodiment of the present invention. More specifically, FIG. 37 views the device 70 from a narrowest side of a gap 73.

As illustrated in FIGS. 35 to 37, the device 70 includes: a third flat plate 71 as one example of the first member; and a fourth flat plate 72 as one example of the second member. The fourth flat plate 72 is obliquely superposed on the third flat plate 71, with the gap 73 formed between the third flat plate 71 and the fourth flat plate 72 in a manner such as to become continuously narrower. Upon irradiation of the device 70 with a predetermined light beam, an interference fringe is caused to appear by the gap 73. A material capable of causing such an interference fringe to appear is selected as a material of the third flat plate 71 and the fourth flat plate 72. For example, a glass plate or a plastic plate is used as a material of the third flat plate 71 and the fourth flat plate 72.

The device 70 includes: inlet height adjusting members 74 as one example of a first height adjusting member; and outlet height adjusting members 75 as one example of a second height adjusting member. The inlet height adjusting members 74 and the outlet height adjusting members 75 are fixed to the third flat plate 71. The inlet height adjusting members 74 are provided on one end side of the gap 73 (an inlet side of a flow channel), and sets a height of the one end of the gap 73. The outlet height adjusting members 75 are provided on another end side of the gap 73 (an outlet side of the flow channel), and sets a height of the other end of the gap 73 to be lower than the height of the one end of the gap 73. The height of the one end of the gap 73 is, for example, 50 nm, and the height of the other end of the gap 73 is, for example, 10 nm. In the device 70 according to the present embodiment, the fourth flat plate 72 is fixed to the inlet height adjusting members 74 and the outlet height adjusting members 75 through, for example, bonding.

No limitation is placed on a material of the inlet height adjusting members 74 and the outlet height adjusting members 75 so long as the materials have no influence on a substance delivered into the gap 73. For example, resin such as ultraviolet curable resin can be used as the material of the inlet height adjusting member 74 and the outlet height adjusting member 75. For example, as the material of the inlet height adjusting members 74 and the outlet height adjusting members 75, resin such as ultraviolet curable resin can be used. Moreover, a droplet (liquid) containing the material of the inlet height adjusting members 74 may be discharged to a plate-shaped member (one example of the to-be-processed member) as the material of the third flat plate 71 upon formation of the inlet height adjusting members 74. Similarly, a droplet (liquid) containing the material of the inlet height adjusting members 75 may be discharged to a plate-shaped member as the material of the third flat plate 71 upon formation of the outlet height adjusting members 75. A droplet discharge apparatus (one example of a liquid discharge apparatus) can be used for the droplet discharge. When the droplet discharge apparatus is used, the plate-shaped member as the material of the third flat plate 71 is transported to a droplet discharge region (a liquid discharge region). The droplet discharge apparatus discharges droplets containing the material of the inlet height adjusting members 74. As a result, the inlet height adjusting members 74 are formed. Similarly, the droplet discharge apparatus discharges droplets containing the material of the outlet height adjusting members 75. As a result, the outlet height adjusting members 75 are formed.

For example, an inkjet printer can be used for forming the inlet height adjusting members 74 and the outlet height adjusting members 75. The use of the inkjet printer permits control of the heights of the inlet height adjusting member 74 and the outlet height adjusting members 75 in units of nanometers. In a case where the inkjet printer is used, a maximum value of the heights of the inlet height adjusting members 74 and the outlet height adjusting members 75 can be 200 nm.

The device 70 further includes a pair of side plates 76 as one example of a pressing member. The pair of side plates 76 covers a pair of side surfaces of the gap 73. The side plates 76 are fixed to the third flat plate 71 and the fourth flat plate 72 through, for example, bonding in the device 70 according to the present embodiment. No limitation is placed on a material of the side plates 76 so long as the material has no influence on a substance delivered into the gap 73. For example, resin such as rubber can be used as the material of the side plate 76.

Figure 38:
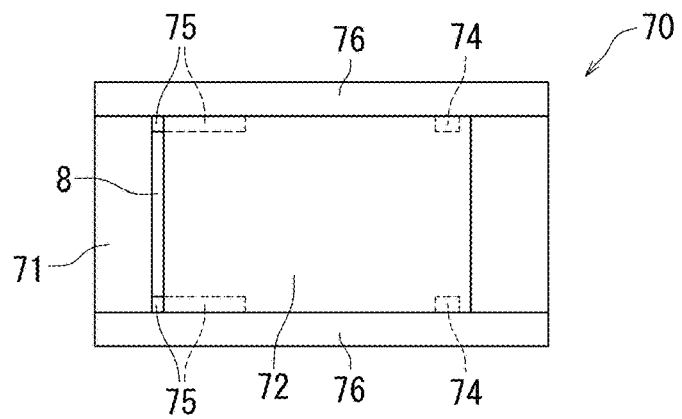
FIG. 38 is a top view schematically illustrating another example of the device according to the ninth embodiment of the present invention.

FIG. 38 is a top view schematically illustrating another example of a device 70 according to the ninth embodiment of the present invention. As illustrated in FIG. 38, the device 70 can include a liquid absorbent substance 8 as is the case with the third embodiment. The liquid absorbent substance 8 is provided outside of a gap 73 adjacently to another end of the gap 73.

Through the above, the ninth embodiment has been described. According to the ninth embodiment, it is possible to set an angle θ of the wedge-shaped gap 73, which hardly results in variation in a height h of the gap 73 between a plurality of devices 70. Therefore, variation in the devices 1 between different product lots can be suppressed.

Note that, as is the case with the second embodiment, surfaces forming the gap 73 may be subjected to surface modification. An example in which the inlet height adjusting members 74 and the outlet height adjusting members 75 are formed through the droplet (liquid) discharge has been described, although the present invention is not limited thereto. For example, the inlet height adjusting members 74 and the outlet height adjusting members 75 can be formed by attaching a material such as glass or acrylic resin thereto. Alternatively, either of the inlet height adjusting members 74 and the outlet height adjusting members 75 may be formed by attaching the material such as glass or an acrylic resin thereto. Alternatively, a height adjusting member may be formed which has a height becoming increasingly lower from one end to the other end of the gap 73. In this case, a portion of the height adjusting member on the one end side of the gap 73 corresponds to the inlet height adjusting members 74. A portion of the height adjusting member on the other end side of the gap 73 corresponds to the outlet height adjusting members 75. Specifically, a method for producing the device 70 includes a process of forming the inlet height adjusting members 74 and the outlet height adjusting members 75 on a plate-shaped member as the material of the third flat plate 71. The method for producing the device 70 also includes a process of preparing a material of the inlet height adjusting members 74 and a material of the outlet height adjusting members 75. The side plates 76 are used in the present embodiment, but the side surfaces of the gap 73 may be covered by, for example, bonding resin.

(Tenth Embodiment)

Figure 39:
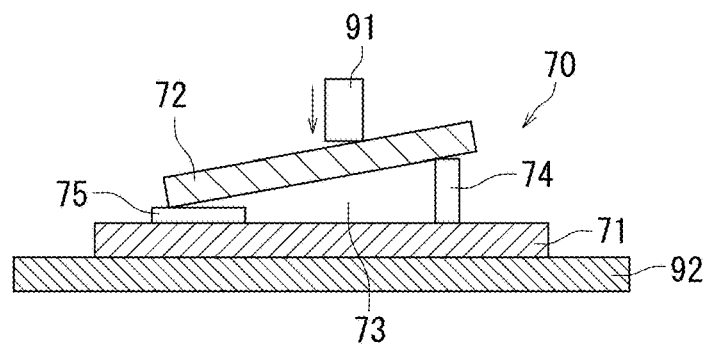
FIG. 39 is a cross-sectional view schematically illustrating one example of a fixation method according to a tenth embodiment of the present invention.
Figure 40:
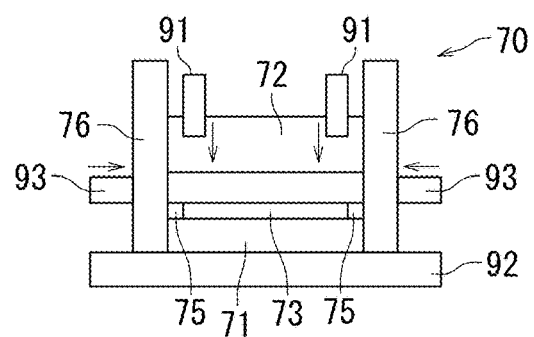
FIG. 40 is a rear view schematically illustrating one example of the fixation method according to the tenth embodiment of the present invention.

Hereinafter, the tenth embodiment will be described, focusing on only a point different from that of the ninth embodiment. The tenth embodiment differs from the ninth embodiment only in that a fourth flat plate 72 and side plate 76 are detachable. FIG. 39 is a cross-sectional view schematically illustrating one example of a fixation method according to the tenth embodiment of the present invention, and FIG. 40 is a rear view schematically illustrating one example of the fixation method according to the tenth embodiment of the present invention. Note that the side plates 76 are omitted for easier understanding.

As illustrated in FIG. 39, a device 70 is loaded on a support base 92 upon causing an interference fringe 60 to appear and delivery of particulates 51 into a gap 73. At this point, the fourth flat plate 72 is pressed against a third flat plate 71. As a result, the fourth flat plate 72 is fixed. The pressing of the fourth flat plate 72 is executed by a driving apparatus 91 such as a piezoelectric element.

As illustrated in FIG. 40, the device 70 is held by a pair of holding members 93 upon causing the interference fringe 60 to appear and the delivery of the particulates 51 into the gap 73. More specifically, the pair of holding members 93 are opposite to each other, and a gap between the pair of the holding members 93 is controlled whereby a pair of the side plates 76 are each pressed toward a center of the device 70. As a result, the pair of side plates 76 are fixed. The pair of holding members 93 can be, for example, a pair of arm parts having a robot arm.

Through the above, the tenth embodiment has been described. To observe the particulates 51 by using the device 70 according to the tenth embodiment, after the particulates 51 are delivered into the gap 73, the fixation of the fourth flat plate 72 and the side plates 76 is released and the fourth flat plate 72 and the side plates 76 are detached from the third flat plate 71. At this point, the particulates 51 delivered into the gap 73 adhere to at least one of the third flat plate 71 and the fourth flat plate 72. Therefore, moving one or both of the third flat plate 71 and the fourth flat plate 72 to an observation position of an electronic microscope (for example, a position opposite to the objective lens 106 included in the particle size measurement apparatus 100 described with reference to FIG. 9 or 31) makes it possible to perform observation of the particulates 51.

Note that, in the present embodiment, since the fourth flat plate 72 is pressed against the third flat plate 71, the fourth flat plate 72 may be bent, even in which case particle sizes of the particulates 51 can accurately be measured by using the interference fringe 60.

Moreover, the fourth flat plate 72 is pressed against the third flat plate 71 in the present embodiment. Thus, depending on a material used for the inlet height adjusting members 74 and the outlet height adjusting members 75, heights of the inlet height adjusting members 74 and the outlet height adjusting members 75 vary when the fourth flat plate 72 is pressed. Therefore adjusting a pressure for pressing the fourth flat plate 72 makes it possible to control a height of the gap 73.

(Eleventh Embodiment)

Figure 41:
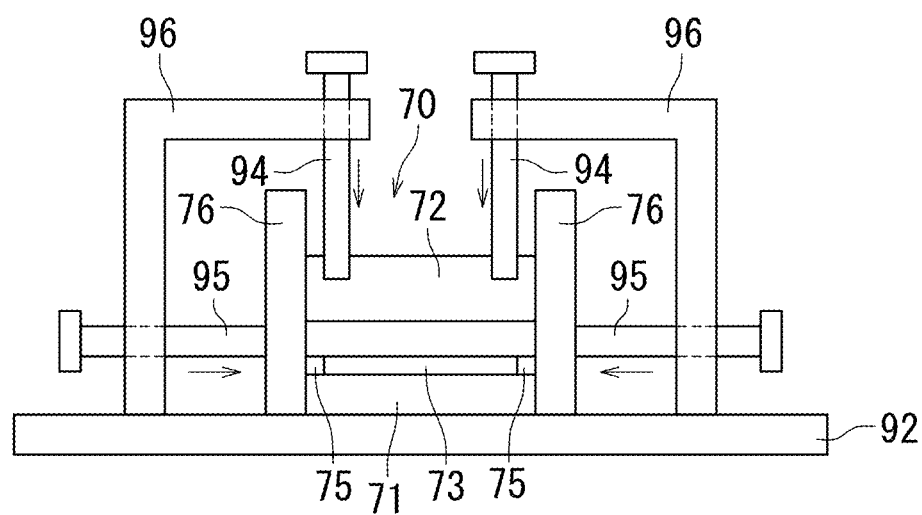
FIG. 41 is a rear view schematically illustrating one example of a fixation method according to an eleventh embodiment of the present invention.

Hereinafter, the eleventh embodiment will be described, focusing on only a point different from that of the tenth embodiment. The eleventh embodiment differs from the tenth embodiment only in a method of fixing a fourth flat plate 72 and side plates 76. FIG. 41 is a rear viewp0 schematically illustrating one example of a fixation method according to the eleventh embodiment of the present invention.

As illustrated in FIG. 41, screws 94 and screws 95 are used for the fixation of the fourth flat plate 72 and the side plates 76 in the eleventh embodiment. The screws 94 are screwed into screw holes formed at frames 96. The frames 96 support the screws 94 in a manner such that tip parts of the screws 94 are projected toward the fourth flat plate 72. Turning the screws 94 brings the tip parts of the screws 94 to abut the fourth flat plate 72 whereby the fourth flat plate 72 is pressed against the third flat plate 71. Moreover, turning the screws 94 can adjust a pressure for pressing the fourth flat plate 72. Similarly, the screws 95 are screwed into screw holes formed at the frames 96. The frames 96 support the screws 95 in a manner such that tip parts of the screws 95 are projected toward the side plates 76. Turning the screws 95 brings the tip parts of the screws 95 to abut the side plates 76 whereby the side plates 76 are pressed toward a center of the device 70. Moreover, turning the screws 95 permits adjustment of a pressure for pressing the side plates 76.

Through the above, the eleventh embodiment has been described. According to the eleventh embodiment, with simple configuration, the fourth flat plate 72 and the side plates 76 can be fixed upon causing an interference fringe 60 to appear and upon the delivery of particulates 51 into a gap 73.

(Twelfth Embodiment)

Figure 42:
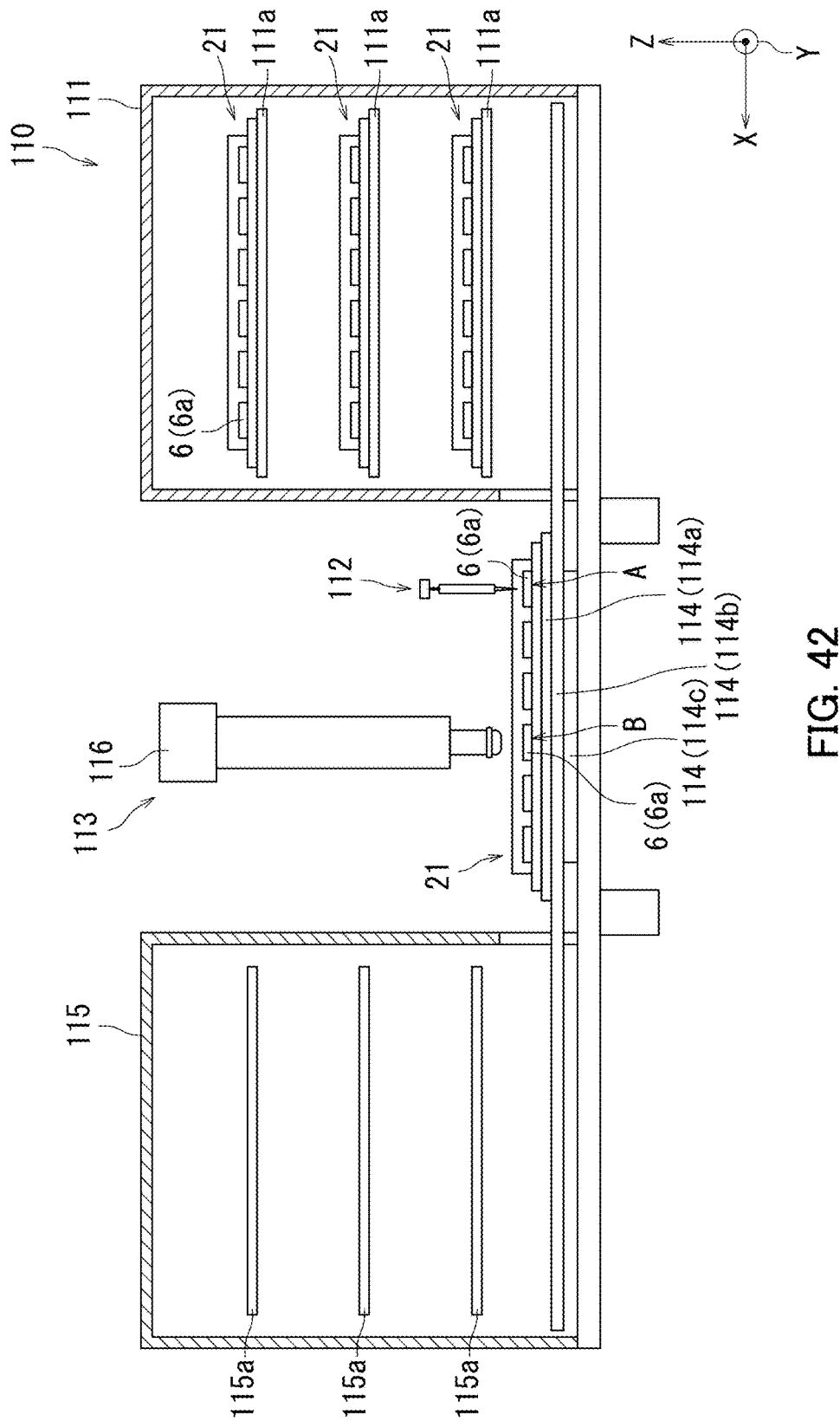
FIG. 42 is a schematic view illustrating an outline of configuration of an automatic observation apparatus according to a twelfth embodiment of the present invention.

Hereinafter, an embodiment of an automatic observation apparatus according to the present invention will be described. FIG. 42 is a schematic view illustrating an outline of configuration of the automatic observation apparatus 110 according to the twelfth embodiment of the present invention. As illustrated in FIG. 42, the automatic observation apparatus 110 includes: a device rack 111, an automatic injector 112, an observing optical system 113, a conveyance mechanism 114, and a used device rack 115. Note that FIG. 42 illustrates a cross section of the device rack 111 and a cross section of the used device rack 115.

The device rack 111 stores the device 21. The device rack 111 may be capable of storing a plurality of devices 21. Note that, in the twelfth embodiment, the automatic observation apparatus 110 conveys the device 21 according to the sixth embodiment or the seventh embodiment to photograph particulates 51, but the present invention is not limited thereto. The automatic observation apparatus 110 may convey the devices 1 according to the first to fifth embodiments and the device 70 according to the ninth embodiment to photograph the particulates 51.

The automatic injector 112 is arranged in correspondence with a predetermined solution injection position A, and a prescribed amount of a solution 50 including particulates 51 and a solvent 52 is injected sequentially to a plurality of gaps 6 formed in the device 21. More specifically, the automatic injector 112 sequentially drips the solution 50 to a plurality of solution introduction parts 7 formed in the device 21.

The observing optical system 113 is arranged in correspondence with a predetermined observation position B and sequentially photographs the plurality of gaps 6 formed in the device 21. As a result, the particulates 51 in each gap 6 are photographed. The observing optical system 113 includes a camera 116. The camera 116 photographs the gap 6 arranged in correspondence with the predetermined observation position B. The observing optical system 113 may include an objective lens (not illustrated). In this case, the camera 116 photographs the gap 6 through the objective lens.

In the ninth embodiment, the conveyance mechanism 114 is a XY stage. That is, the conveyance mechanism 114 includes a conveyance stand 114a, an X stage 114b, and a Y stage 114c. The X stage 114b and the Y stage 114c are so configured as to be capable of conveying the conveyance stand 114a in an X-direction and a Y-direction. Note that the conveyance mechanism 114 is not limited to the XY stage. For example, the conveyance mechanism 114 may be a XYZ stage. Alternatively, a conveyor mechanism may be used as the conveyance mechanism 114.

Upon loading of the device 21 on the conveyance stand 114a in the device rack 111, the conveyance mechanism 114 conveys the device 21 (the conveyance stand 114a) in a manner such that the gaps 6 of the device 21 sequentially stop at the predetermined solution injection position A. The automatic injector 112 sequentially injects the solution 50 to the gaps 6 stopping at the predetermined solution injection position A. The conveyance mechanism 114 also conveys the device 21 (the conveyance stand 114a) in a manner such that the gaps 6 of the device 21 sequentially stop at the predetermined observation position B. The observing optical system 113 sequentially photographs the gaps 6 stopping at the predetermined observation position B. The conveyance mechanism 114 conveys the device 21 into the used device rack 115 upon completion of the photographing of all the gaps 6. The used device rack 115 stores the device 21 that has already been photographed. The used device rack 115 may be capable of storing a plurality of devices 21.

Note that the device rack 111 is provided with support stands 111a, and a conveyance mechanism (not illustrated) for moving the device 21 from the support stand 111 to the conveyance stand 114a is provided in the device rack 111. The conveyance mechanism includes an elevation mechanism. Similarly, the used device rack 115 is provided with support stands 115a, and a conveyance mechanism (not illustrated) for moving the device 21 from the conveyance stand 114a to the support stand 115a is provided in the used device rack 115. The conveyance mechanism includes an elevation mechanism.

To inject the solution 50 to one or some of all the gaps 6 of the device 21, the conveyance mechanism 114 may convey the device 21 (the conveyance stand 114a) in a manner such that only the gap 6 targeted for the solution injection stops at the predetermined solution injection position A. In this case, the conveyance mechanism 114 may convey the device 21 (the conveyance stand 114a) in a manner such that only the gap 6 into which the solution has been injected stops at the predetermined observation position B.

Note that the observing optical system 113 may irradiate a light beam toward the gap 6 stopping at the predetermined observation position B to cause an interference fringes 60 to appear. In this case, the observing optical system 113 may include a light source 103, a filter 104, a mirror 105, and an objective lens 106, as is the case with the particle size measurement apparatus 100 described with reference to FIG. 9. Further, the automatic observation apparatus 110 may include an analysis section 102, as is the case with the particle size measurement apparatus 100 described with reference to FIG. 9. This permits analysis of particle sizes of the particulates 51 by the analysis section 102.

Moreover, as described in the eighth embodiment, the observing optical system 113 may have configuration such that a plurality of light beams having different wavelengths can be irradiated toward the gap 6 stopping at the predetermined observation position B. This makes it possible to accurately determine how many dark lines there are before an observed dark line, as described in the eighth embodiment. In photographing the particulates 51, one of the plurality of light beams is used.

Through the above, the twelfth embodiment has been described. According to the twelfth embodiment, the device 21 is automatically taken out from the device rack 111. Moreover, the solution 50 is automatically dripped to the device 21 by the automatic injector 112. Moreover, the particulates 51 in each gap 6 are automatically photographed. Then the device 21 is automatically stored into the used device rack 115. Therefore, automation of observation (the photographing) of the particulates 51 can be realized.

The automatic observation apparatus 110 may be configured such that a predetermined reaction liquid is injected into the gap 6 by the automatic injector 112 after introduction of the particulates 51 into the gap 6. This can automate verification of resistance of the particulates 51 against the predetermined reaction liquid and verification of chemical reaction of the particulates 51 against the predetermined reaction liquid.

The particulates 51 remain in the device 21 stored in the used device rack 115. Therefore, covering an inlet and an outlet of the gap 6 after the storage of the device 21 in the used device rack 115 permits preservation of the particulates 51. Therefore, an operation of preserving the particulates 51 can be half-automated by the automatic observation apparatus 110. Further, the automatic observation apparatus 110 may be configured such that a predetermined preservative solution is injected into the gap 6 by the automatic injector 112 after introduction of the particulates 51 into the gap 6.

The automatic observation apparatus 110 is applicable to devices other than the devices 1, 21, and 70. For example, the devices 30a to 30c described with reference to FIGS. 31 to 33 may be used as devices conveyed by the automatic observation apparatus 110. That is, any device conveyed by the automatic observation apparatus 110 may be a device which has a clearance portion becoming continuously smaller and which causes an interference fringe to appear by the clearance portion, or may be a device which has a clearance portion becoming continuously smaller and which is capable of trapping particulates in the clearance portion.

Through the above, the first to twelfth embodiments have been described. Note that the points described in the embodiments can be combined as appropriate.

INDUSTRIAL APPLICABILITY

The present invention is preferably applicable to particle size measurement of particulates, verification of resistance of particulates against physical stress, verification of resistance of particulates against a predetermined reactive fluid, verification of chemical reaction of particulates to a predetermined reactive fluid, particulate preservation, automation of particulate observation, etc.

REFERENCE SIGNS LIST

1 Device
2 First plate-shaped member
3 Second plate-shaped member
3a Plate-shaped member 5 Groove
5a Inclined surface
6 Gap
8 Liquid absorbent substance
21 Device
30a Device
31a First flat plate
32a Second flat plate
33a Gap
30b Device
31b Lens
32b Flat plate 60
33b Gap
30c Device
31c Flat plate
32c Lens
33c Gap
42 Driving element
43 Tool
50 Solution
51 Particulates
52 Solvent
60 Interference fringe
70 Device
71 Third flat plate
72 Fourth flat plate
73 Gap
74 Inlet height adjusting member
75 Outlet height adjusting member
76 Side plate
100 Particle size measurement apparatus
101 Observing optical system
102 Analysis section
103, 103a, 103b Light source
106 Objective lens
107 Camera
110 Automatic observation apparatus
111 Device rack
112 Automatic injector
113 Observing optical system
114 Conveyance mechanism
115 Used device rack
116 Camera

The invention claimed is:

1. A device comprising:
a first member, and
a second member forming a gap together with the first member, wherein
the gap has one end and another end, the one end being wider than the other end,
the second member is superposed on the first member,
the second member has an opposite surface opposite to the first member,
the opposite surface has a groove that forms the gap,
the groove extends from the one end toward the other end of the gap,
the groove is configured to generate interference fringes in the gap upon irradiation of the gap with a plurality of monochromatic light beams having different wavelengths, the interference fringes appearing for the respective monochromatic light beams,
portions of the opposite surface located on respective opposite sides of the groove are in contact with the first member,
the first member has a longer length than the second member in a direction in which the groove extends, and
the first member has a portion extending outward of the one end in the direction in which the groove extends.

2. An automatic observation apparatus comprising:
an automatic injector being arranged in correspondence with a predetermined solution injection position, the automatic injector injecting a solution, including particles and a solvent, into the gap included in the device according to claim 1;
an observing optical system being arranged in correspondence with a predetermined observation position; and
a conveyance mechanism conveying the device in a manner such that the gap stops at the solution injection position and then conveying the device in a manner such that the gap stops at the observation position.

3. The automatic observation apparatus according to claim 2, wherein
the observing optical system obtains an image of particles present in the gap by photographing the gap.

4. The device according to claim 1, wherein
a bottom surface of the groove includes an inclined surface, and
the gap including a flow channel is formed by superposing the second member on the first member in a manner such that the inclined surface faces the first member.

5. The device according to claim 1, wherein at least part of surfaces forming the gap is subjected to surface modification.

6. The device according to claim 5, wherein
the surface modification imparts an anionic property, a cationic property, a hydrophobic property, or a hydrophilic property to the at least part of the surfaces forming the gap.

7. The device according to claim 1, further comprising a liquid absorbent substance provided outside of the other end of the gap, the liquid absorbent substance including a substance that absorbs a liquid, wherein
the liquid absorbent substance has a surface constituting a boundary surface with air surrounding the liquid absorbent substance.

8. A method for measuring a particle size of a particle by using the device according to claim 1, the method comprising:
delivering the particle into the gap included in the device from the one end of the gap, moving the particle toward the other end of the gap, and trapping the particle in the gap; and
measuring a particle size of the trapped particle based on the interference fringe caused to appear by the gap.

9. The method for measuring a particle size of a particle according to claim 8, wherein
in the trapping the particle in the gap, the particle is trapped at a portion of the gap in accordance with a size of the particle, the portion of the gap being a portion having a height corresponding to the size of the particle.

10. The method for measuring a particle size of a particle according to claim 8, wherein
the measuring a particle size of the trapped particle includes measuring a height of the gap at a position where the particle is trapped as the particle size of the trapped particle.

11. The method for measuring a particle size of a particle according to claim 8, wherein
the interference fringe repeatedly has a bright line and a dark line in a direction of extension of the gap, and
in the measuring a particle size of the trapped particle, the particle size of the trapped particle is measured based on how many dark lines or bright lines there are as counted from the other end of the gap before a dark line or a bright line appearing at a position corresponding to a position where the particle is trapped.

12. A method for observing resistance of a particle by using the device according to claim 1, the method comprising:
   delivering the particle into the gap included in the device from the one end of the gap and moving the particle toward the other end of the gap; and
   adding physical stress to the particle present in the gap or injecting a predetermined reactive fluid from the one end into the gap.

13. A method for causing chemical reaction of a particle by using the device according to claim 1, the method comprising:
   delivering the particle into the gap included in the device from the one end of the gap and moving the particle toward the other end of the gap; and
   injecting a predetermined reactive fluid from the one end into the gap.

14. A method for preserving a particle by using the device according to claim 1, the method comprising:
   delivering the particle into the gap included in the device from the one end of the gap and moving the particle toward the other end of the gap; and
   covering the one end and the other end of the gap.

15. The device according to claim 1, wherein
   the gap is configured to suck a solvent including particles from the one end into the gap through a capillary action, and move the particles from the one end to the other end of the gap by using, as a driving force, a force for sucking the solvent into the gap.

16. The device according to claim 1, wherein
   the second member has a plurality of the grooves arranged along a direction orthogonal to a direction of extension of the grooves, and
   the second member forms a plurality of the gaps together with the first member.

17. The device according to claim 1, comprising a plurality of the second members, the second members each forming the gap together with the first member.

18. A method for measuring a height or a thickness of a measurement target based on an interference fringe caused to appear on the measurement target, the method comprising:
   irradiating the measurement target with a plurality of monochromatic light beams having different wavelengths to cause interference fringes for the respective monochromatic light beams to appear on the measurement target;
   obtaining a position where dark lines of the interference fringes for the respective monochromatic light beams overlap; and
   determining positions of first dark lines of the interference fringes for the respective monochromatic light beams based on half-wavelengths of the respective monochromatic light beams, a common multiple of the half-wavelengths of the respective monochromatic light beams, and the position where the dark lines of the interference fringes for the respective monochromatic light beams overlap.

19. A method for producing a device including a first member and a second member forming a gap together with the first member,
   the second member of the device having a flow channel having an inclined surface, and the gap including the flow channel being formed by superposing the second member on the first member in a manner such that the inclined surface faces the first member,
   the method comprising:
      adjusting a height of one end of a to-be-processed member by a piezoelectric element to incline the to-be-processed member;
      fabricating the second member by carrying out, at least once, cutting the to-be-processed member by moving a tool horizontally with respect to the inclined to-be-processed member to form the flow channel; and
      cleaning at least respective portions of the first member and the second member that form the gap.

20. An observation apparatus comprising an observing optical system that obtains an image of a measurement target present in a gap included in a device, wherein
   the observing optical system is configured to
      irradiate the gap with a plurality of monochromatic light beams having different wavelengths to cause interference fringes for the respective monochromatic light beams to appear in the gap, and
      obtain an image of the interference fringes for the respective monochromatic light beams, and
   the observation apparatus further comprises an analysis section configured to
      obtain a position where dark lines of the interference fringes overlap from the image of the interference fringes for the respective monochromatic light beams, and
      determine positions of first dark lines of the respective interference fringes based on half-wavelengths of the respective monochromatic light beams, a common multiple of the half-wavelengths of the respective monochromatic light beams, and the position where the dark lines of the respective interference fringes overlap.

* * * * *